(12) United States Patent
Luu et al.

(10) Patent No.: US 7,893,304 B2
(45) Date of Patent: Feb. 22, 2011

(54) HYDROQUINONE LONG-CHAIN DERIVATIVES AND/OR PHENOXY LONG-CHAIN DERIVATIVES, AND PHARMACEUTICALS COMPRISING THE SAME

(75) Inventors: Bang Luu, Strasbourg (FR); Dominique Bagnard, Strasbourg (FR); Mazen Hanbali, Strasbourg (FR); Masashi Yamada, Tokyo (JP); Hiroto Suzuki, Tokyo (JP)

(73) Assignee: Meiji Dairies Corporation, Tokyo (JP)

( * ) Notice: Subject to any disclaimer, the term of this patent is extended or adjusted under 35 U.S.C. 154(b) by 138 days.

(21) Appl. No.: 11/816,625

(22) PCT Filed: Feb. 23, 2006

(86) PCT No.: PCT/JP2006/303272

§ 371 (c)(1),
(2), (4) Date: Aug. 18, 2008

(87) PCT Pub. No.: WO2006/093014

PCT Pub. Date: Sep. 8, 2006

(65) Prior Publication Data

US 2009/0036542 A1      Feb. 5, 2009

(30) Foreign Application Priority Data

Feb. 28, 2005   (JP) .............................. 2005-054012

(51) Int. Cl.
  C07C 43/205    (2006.01)
  C07C 215/68    (2006.01)
  A61K 31/045    (2006.01)
  A61K 31/09     (2006.01)

(52) U.S. Cl. ....................... 568/648; 568/658; 564/443; 514/646; 514/718

(58) Field of Classification Search ........................ None
See application file for complete search history.

(56) References Cited

U.S. PATENT DOCUMENTS

| 4,252,951 A * | 2/1981 | Jackson et al. .............. 540/220 |
| 4,271,083 A | 6/1981 | Morimoto et al. |
| 5,059,627 A | 10/1991 | Goto et al. |
| 2007/0027299 A1 | 2/2007 | Morishita et al. |

FOREIGN PATENT DOCUMENTS

| FR | 2246528 | 5/1975 |
| GB | 2055097 | 2/1981 |
| JP | 52-128130 | 10/1977 |
| JP | 53-46029 | 4/1978 |
| JP | 61-40236 A | 2/1986 |
| JP | 1-311076 A | 12/1989 |
| JP | 2-101036 A | 4/1990 |
| JP | 2-207254 A | 8/1990 |
| JP | 4-145036 A | 5/1992 |
| JP | 4-182446 A | 6/1992 |
| JP | 4-210643 A | 7/1992 |
| JP | 6140236 | 5/1994 |
| JP | 2003-502317 A | 1/2003 |
| WO | WO 91/11994 A1 | 8/1991 |
| WO | WO 93/02031 A1 | 2/1993 |
| WO | WO 99/08987 | 2/1999 |
| WO | WO 99/08987 A1 | 2/1999 |
| WO | WO 2004/092245 | 10/2004 |

OTHER PUBLICATIONS

Database CAPLUS on STN, Acc. No. 1954:35910, Shulgin et al., Journal of the Chemical Society (1953), p. 1316-1318 (abstract).*
Braga et al., Chem. Commun. (2005), 29, p. 3635-3645.*
Database CAPLUS on STN, Acc. No. 2000:471169, Hoppen et al., Angewandte Chemie, International Edition (2000), 39(12), p. 2099-2102 (abstract).*
Database CAPLUS on STN, Acc. No. 1978:191082, Vig et al., Indian Journal of Chemistry, Section B: Organic Chemistry Including Medicinal Chemistry (1977), 15B(11), p. 988-990 (abstract).*
Takeuchi et al., "Stimulation of nerve growth factor synthesis/secretion by 1,4-benzoquinone and its derivatives in cultured mouse astroglial cells," FEBS Letters, Feb. 12, 1990, vol. 261, No. 1, pp. 63-66.
Armstrong et al. "The introduction of n-alkyl groups into phenols and hydroquinones"*J. Am. Chem. Soc.*, 1960, pp. 1928-1935, vol. 82, No. 8.
Barclay et al. "Chain-breaking phenolic antioxidants: Steric and electronic effectsin polyayalkylchromanols, tocopherol analogs, hydroquinones, and superior antioxidants of the polyalkylbenzochromanol and naphthofuran class" *J. Org. Chem.*, 1993, pp. 7416-7420, vol. 58, No. 26.
Database CA, Database Accession No. 107:59573, Ringsdorf et al. "Synthesis, structure, and phase behavior of liquid crystalline rigid-rod polyesters and polyamides with disc-like mesogens in the main chain" 1987, Chemical Abstracts Service, Columbus, Ohio, US; pp. 6.
Database CA, Database Accession No. 111:148997, Morimoto of al., "Ubiquinone and related compounds. XL. Synthesis and biochemical behavior of idebenone and related compounds" 1989, Chemical Abstracts Service, Columbus, Ohio, US; pp. 276.
Database CA, Database Accession No. 145:489416, Li et al. "First total synthesis of 5-methyl-2-(2E, 6E-3,7,11-trimethyl-9-oxo-2,6-dodecadienyl)benzo-1,4-quinone and the corresponding hydroquinone", 2005, Chemical Abstracts Service, Columbus, Ohio, US: pp. 786.

(Continued)

*Primary Examiner*—Brian J Davis
(74) *Attorney, Agent, or Firm*—Saliwanchik, Lloyd & Eisenschenk

(57) ABSTRACT

The present invention provides compounds that are useful for preventing or treating brain dysfunctions, motor dysfunctions, or urinary dysfunctions caused by the degeneration and/or loss of the central nervous system or peripheral nervous system cells.

17 Claims, 6 Drawing Sheets

OTHER PUBLICATIONS

Gonzalez de Aguilar et al. "Neurotrophic activity of 2, 4, 4-trimethyl-3-(15-hydroxypentadecyl)-2-cyclohexen-1-one-in cultured central nervous system neurons" *Brain Res.*, 2001, pp. 65-73, vol. 920, Nos. 1-2.

Hoppen et al., "Natural-Product Hybrids: Design, Synthesis, and Biological Evaluation of Quinone—Annonaceous Acetogenins," *Angew. Chem. Int. Ed.*, 2000, pp. 2099-2102, vol. 39, No. 12.

Inouye et al. "Components of pirolacae. XV. Structure of pyrolatin" *Chemische Berichte*, 1968, pp. 4057-4065, vol. 101, No. 12.

McPhail et al. "Sequestered chemistry of the arminacean nudibranch leminda millecra in Algoa Bay, South Africa" *J Nat Prod.*, 2001, pp. 1183-1190, vol. 64, No. 9.

Muller of al. "Tocopherol long chain fatty alcohols decrease the production of TNF-alpha and NO radicals by activated microglial cells" *Bioorg Med Chem Lett.*, 2004, pp. 6023-6026, vol. 14, No. 24.

Rodriguez-Parada et al. "A comparative study of mesophase formation in rigid-chain polyesters with flexible side chains" *Macromolecules*, 1989, pp. 2507-2516, vol. 22, No. 5.

Sasaki et al. "Synthesis of [11c] coenzyme q-related compounds for in vivo estimation of mitochondrial electron transduction and redox state in brain" *Nucl Med Biol.*, 1999, pp. 183-187, vol. 26, No. 2.

Yu at al. "Synthesis and Properties of polyamides and polyester on the basis of 2,2'—bipyridine-5,5'-dicarboxylic acid and the corresponding polymer-ruthenium complexes" *Macromolecules*, 2000, pp. 3259-3273, vol. 33, No. 9.

Morimoto et al., "Ubiquinone and related compounds. XL. Synthesis and biochemical behavior of idebenone and related compounds" 1989, *Naturwissenschaften*, pp. 200-205, vol. 76, No. 5.

\* cited by examiner

CONTROL

QFA15 (1nM)

HYDROQUINONE LONG-CHAIN DERIVATIVES AND/OR PHENOXY LONG-CHAIN DERIVATIVES, AND PHARMACEUTICALS COMPRISING THE SAME

This application is a National Stage Application of International Application Number PCT/JP2006/303272, filed Feb. 23, 2006; which claims priority to JP 2005-054012, filed Feb. 28, 2005.

TECHNICAL FIELD

The present invention relates to hydroquinone long-chain derivatives and/or phenoxy long-chain derivatives, and pharmaceuticals comprising such derivatives. In particular, the present invention relates to hydroquinone long-chain derivatives and/or phenoxy long-chain derivatives (hereinafter, they may be collectively referred to as "hydroquinone long-chain derivatives") that have excellent antioxidative activity and/or neurite-extension activity and are useful as preventive or therapeutic agents for brain dysfunctions, and peripheral nervous system disorders such as paralysis and hyperalgesia or hypoalgesia, which are induced by degeneration, loss, or damage of central nervous system neurons such as brain cells and/or peripheral nervous system neurons; and pharmaceuticals comprising these derivatives.

BACKGROUND ART

Alzheimer-type dementia, or alternatively Parkinson's disease, is a brain dysfunction caused by degeneration or loss of neurons. Brain dysfunctions a also caused by degeneration or loss of neurons due to cerebral infarction, cerebral apoplexy, or such.

Alzheimer-type dementia is treated by treatments using cholinesterase inhibitors or muscarinic receptor agonists. For Parkinson's disease, dopamines or dopamine-like agonists are administered. However, treatments using such pharmaceutical agents are symptomatic treatments, and although the symptoms improve temporarily, they neither stop nor delay the progress of the pathological condition. There is also no therapeutic method aimed at completely curing brain dysfunctions caused by cerebral infarction, cerebral apoplexy, or such.

Multiple sclerosis presents symptoms such as lightheadedness, blurry vision, double vision, dysuria, pain, numbness, and epilepsy. Although their cause is not known, these symptoms are considered to develop due to the degeneration or loss of neurons of the central nervous system such as the cerebrum, midbrain, cerebellum, medulla oblongata, spinal cord, or optic nerve. There are also cases in which the neurons of the peripheral nervous system are degenerated or lost. Therapeutic methods involve administration of steroid agents, interferons, or immunosuppressive agents. However, all of these pharmaceutical agents only delay the progress of the pathological condition, and do not provide a complete cure.

Motor paralysis such as amyotrophic lateral sclerosis is a disease in which voluntary movement is impossible due to the impairment of motor nerves ranging from the motor center to the muscles. Paralysis due to impairment of the upper motor nerve ranging from the cerebrum to the spinal anterior horn cells is called central paralysis; that due to impairment of the lower nerve ranging from the spinal anterior horn cells to the muscles is called peripheral paralysis. Depending on the location, motor paralysis can be categorized into monoplegia (paralysis of only one limb), hemiplegia (unilateral upper and lower limb paralysis), paraplegia (paralysis of both lower limbs), and quadriplegia. Therapeutic methods that match the symptoms of each individual (such as rehabilitation and nerve transplantation) are carried out, but complete functional recovery is difficult and treatment takes a long time.

Diabetes or lower urinary tract diseases such as prostatic hyperplasia lead to loss or degeneration of neurons of the bladder or around the bladder, and then urinary dysfunctions such as over- or underactive bladder are caused by imbalances between urine collection and urination. Urinary function may also become abnormal when the urination center is damaged by cerebral infarction, cerebral apoplexy, or such. Urinary dysfunctions such as frequent urination, polyuria, and residual urine significantly lower a patient's "quality of life" (QOL), and are considered clinically important problems. These dysfunctions are treated by symptomatic treatments using anticholinergic agents in combination with treatments of the causative diseases.

Neuralgia such as cancer pain, diabetic pain, and trigeminal neuralgia is called neurogenic pain, and is intractable pain. The causative diseases are treated and pain relief using analgesic agents or local anesthesia is carried out, but there are no methods that directly treat the injured neurons. Furthermore, since diabetes damages nerves throughout the body, it induces neuropathies such as sensory paralysis.

Cyclohexenone long-chain alcohol compounds are known to have neuronal growth-promoting activity (for example, Patent Document 1). However, if compounds with better activity can be provided, they would be useful.
[Patent Document 1] WO99/08987

DISCLOSURE OF THE INVENTION

Problems to be Solved by the Invention

Therefore, an objective of the present invention is to provide compounds that improve various neurogenic diseases by directly acting on neurons and protecting cells and promoting nerve growth.

Means for Solving the Problems

In view of the above circumstances, the present inventors carried out various studies on low-molecular-weight compounds having antioxidative activity or nerve growth promoting activity. Hydroquinone long-chain derivatives are known to have a powerful ability to scavenge free radicals and have biochemical effects of interest. The present inventors screened a series of hydroquinone long-chain derivatives using a primary cell culture and a model for axonal growth of neurons. This screening identified a series of compounds that strongly promoted axonal growth and that were non-toxic to biological cells. Research on antioxidative activity using different evaluations of radical scavenging ability revealed that certain types of hydroquinone long-chain derivatives have very strong antioxidative ability.

As a result, the present inventors discovered hydroquinone long-chain derivatives represented by formulas (1) and (2) shown below and completed the present invention.

More specifically, a certain embodiment of the present invention provides the compound represented by formula (1) shown below:

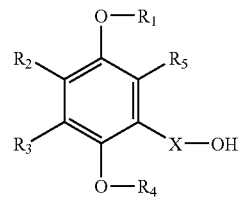

(wherein $R_1$, $R_2$, $R_3$, $R_4$, and $R_5$ are each individually selected from among a hydrogen atom, methyl group, acetyl group, hydroxyl group, and alkoxy group; and X represents an alkylene group or alkenylene group).

The present invention also provides pharmaceutically acceptable salts of the compounds of formula (1) shown above, or solvates or hydrates thereof.

In addition, the present invention provides antioxidants comprising as active ingredients the above-mentioned compounds of formula (1), pharmaceutically acceptable salts thereof, or solvates or hydrates thereof. Alternatively, the present invention relates to uses of the above-mentioned compounds of formula (1), pharmaceutically acceptable salts thereof, or solvates or hydrates thereof for preparing antioxidants.

The present invention also provides nerve growth-promoting agents comprising as active ingredients the above-mentioned compounds of formula (1), pharmaceutically acceptable salts thereof, or solvates or hydrates thereof. Alternatively, the present invention relates to uses of the above-mentioned compounds of formula (1), pharmaceutically acceptable salts thereof, or solvates or hydrates thereof for preparing nerve growth-promoting agents.

Furthermore, the present invention provides pharmaceuticals comprising as active ingredients the above-mentioned compounds of formula (1), pharmaceutically acceptable salts thereof, or solvates or hydrates thereof, which are pharmaceuticals that prevent or treat brain dysfunctions, motor dysfunctions, or urinary dysfunctions caused by degeneration and/or loss of the central nervous system and peripheral nervous system neurons.

Alternatively, the present invention provides therapeutic agents for prevention and/or treatment of dysfunctions caused by degeneration and/or loss of the central nervous system and/or peripheral nervous system neurons, which comprise as active ingredients the above-mentioned compounds of formula (1), pharmaceutically acceptable salts thereof, or solvates or hydrates thereof.

The present invention also relates to uses of the above-mentioned compounds of formula (1), pharmaceutically acceptable salts thereof, or solvates or hydrates thereof for preparing therapeutic agents for prevention and/or treatment of dysfunctions caused by degeneration and/or loss of the central nervous system and/or peripheral nervous system neurons. In addition, the present invention relates to methods for preventing and/or treating dysfunctions, in which the methods comprise the step of administering the above-mentioned compounds of formula (1) to patients who have a dysfunction caused by degeneration and/or loss of the central nervous system and/or peripheral nervous system neurons. Dysfunctions in the present invention include, for example, brain dysfunctions, motor dysfunctions, and urinary dysfunctions.

Another embodiment of the present invention provides compounds represented by formula (2) indicated below, pharmaceutically acceptable salts thereof, or solvates or hydrates thereof:

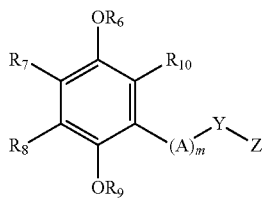

(wherein $R_6$, $R_7$, $R_8$, $R_9$, and $R_{10}$ are each individually selected from among a hydrogen atom, alkyl group, acetyl group, hydroxyl group, and alkoxy group; A represents an oxygen atom or NH, and m is 0 or 1; and Y represents an alkylene group or alkenylene group, and Z represents a hydrogen atom or hydroxyl group).

In the above-mentioned formula (2), $R_6$, $R_7$, $R_8$, $R_9$, and $R_{10}$ are preferably hydrogen atoms.

In the above-mentioned formula (2), preferably, $R_6$, $R_7$, $R_8$, $R_9$, and $R_{10}$ are each a hydrogen atom, m is 0, Y represents an alkylene group with 10 to 20 carbons, and Z is a hydroxyl group.

In the above-mentioned formula (2), preferably, $R_6$ and $R_9$ are each a methyl group, $R_7$ is a methoxy group, $R_8$ and $R_{10}$ are each a hydrogen atom, m is 0, Y is an alkylene group with 10 to 20 carbons, and Z is a hydroxyl group.

In the above-mentioned formula (2), preferably, $R_6$ and $R_9$ are each a methyl group, $R_7$, $R_8$ and $R_{10}$ are each a hydrogen atom, A is an oxygen atom, m is 1, Y is an alkylene group with 10 to 20 carbons, and Z is a hydroxyl group.

In the above-mentioned formula (2), preferably, $R_6$ and $R_9$ are each a methyl group, $R_7$, $R_8$ and $R_{10}$ are each a hydrogen atom, A is NH, m is 1, Y is an alkylene group with 10 to 20 carbons, and Z is a hydroxyl group.

In the above-mentioned formula (2), preferably, $R_6$, $R_7$, $R_8$, $R_9$, and $R_{10}$ are each a hydrogen atom, m is 0, Y is an alkylene group with 10 to 20 carbons, and Z is a hydrogen atom.

In the above-mentioned formula (2), Y is preferably an alkylene group with 12 to 18 carbons.

The present invention also provides antioxidants comprising as active ingredients the above-mentioned compounds of formula (2), pharmaceutically acceptable salts thereof, or solvates or hydrates thereof.

In addition, the present invention provides nerve growth-promoting agents comprising as active ingredients the above-mentioned compounds of formula (2), pharmaceutically acceptable salts thereof, or solvates or hydrates thereof.

The present invention also provides preventive and/or therapeutic agents for brain dysfunctions, motor dysfunctions, or urinary dysfunctions caused by degeneration and/or loss of the central nervous system and peripheral nervous system neurons, which comprise as active ingredients the above-mentioned compounds of formula (2), pharmaceutically acceptable salts thereof, or solvates or hydrates thereof.

Furthermore, the present invention provides methods for preventing and/or treating dysfunctions caused by degeneration and/or loss of the central nervous system and/or peripheral nervous system neurons, in which the methods comprise the step of administering an effective amount of the above-mentioned compounds of formula (2), pharmaceutically acceptable salts thereof, or solvates or hydrates thereof, to patients who have a dysfunction caused by degeneration and/or loss of the central nervous system and/or peripheral nervous system neurons.

The present invention also provides uses of the above-mentioned compounds of formula (2), pharmaceutically acceptable salts thereof, or solvates or hydrates thereof for preparing therapeutic agents for prevention and/or treatment of dysfunctions caused by degeneration and/or loss of the central nervous system and/or peripheral nervous system neurons. Dysfunctions in the present invention include brain dysfunctions, motor dysfunctions, or urinary dysfunctions.

As used herein, the term "pharmaceutically acceptable salts" refers to ordinary salts formed from appropriate non-toxic organic or inorganic acids, or organic or inorganic bases, and which maintain the biological efficacy and properties of the compounds of formula (1) or (2). Examples of acid addition salts include those derived from inorganic acids such as hydrochloric acid, hydrobromic acid, hydroiodic acid, sulfuric acid, sulfamic acid, phosphoric acid, and nitric acid; and those derived from organic acids such as p-toluenesulfonic acid, salicylic acid, methanesulfonic acid, oxalic acid, succinic acid, citric acid, malic acid, lactic acid, fumaric acid, and acetic acid. Examples of base addition salts include those derived from potassium hydroxide, sodium hydroxide, ammonium hydroxide, and quaternary ammonium hydroxide such as tetramethylammonium hydroxide.

The compounds of formula (1) or (2) of the present invention may absorb moisture and then adsorb water or form hydrates when they are left to stand in the atmosphere, and such hydrates are also encompassed in the present invention. Furthermore, the compounds of formula (1) or (2) of the present invention may absorb certain other types of solvents to form solvates, and such solvates are also encompassed in this invention.

As used herein, the term "degeneration" refers to (1) conditions in which cells or tissues are damaged, leading to decreased function, and causing abnormal substances to appear in the cells or in the tissues (between cells); or (2) changes in physical properties of a protein due to heating or a certain type of chemical substance.

As used herein, the term "loss" means that degeneration of cells progresses and causes the cells to die.

As used herein, the term "brain dysfunction" means impairment of brain functions due to degeneration or loss of neurons. More specifically, examples include brain dysfunctions accompanying diseases such as Alzheimer-type dementia, Parkinson's disease, and multiple sclerosis. Therefore, the compounds of the present invention are useful for preventing or treating such diseases.

As used herein, the term "motor dysfunction" means a disorder in which voluntary movement is impaired due to damage of motor neurons extending from the motor center to the muscles. Disorders accompanying such symptoms include, for example, amyotrophic lateral sclerosis.

As used herein, the term "urinary dysfunction" refers to symptoms that arise due to abnormality in urinary functions. Specific examples of the symptoms include frequent urination, polyuria, and residual urine. Compounds of the present invention are useful for alleviation of these symptoms.

The compounds of the present invention are useful for treating or preventing brain dysfunctions, motor dysfunctions, or urinary dysfunctions due to degeneration and/or loss of the central nervous system and/or peripheral nervous system neurons. Specific examples of diseases caused by brain dysfunctions, motor dysfunctions, or urinary dysfunctions include, for example, multiple sclerosis, myasthenia gravis, SMON, amyotrophic lateral sclerosis, dermatomyositis/polymyositis, spinocerebellar degeneration, Parkinson's disease, Huntington's disease, Shy-Drager syndrome, Creutzfeldt-Jakob disease, Behcet's disease, systemic lupus erythematosus, sarcoidosis, peri arteritis nodosa, amyloidosis, ossification of posterior longitudinal ligament, occlusive disease in circle of Willis, diffuse spinal canal stenosis, mixed connective tissue disease, muscular dystrophy, and Alzheimer's disease.

BEST MODE FOR CARRYING OUT THE INVENTION

Figure 1:
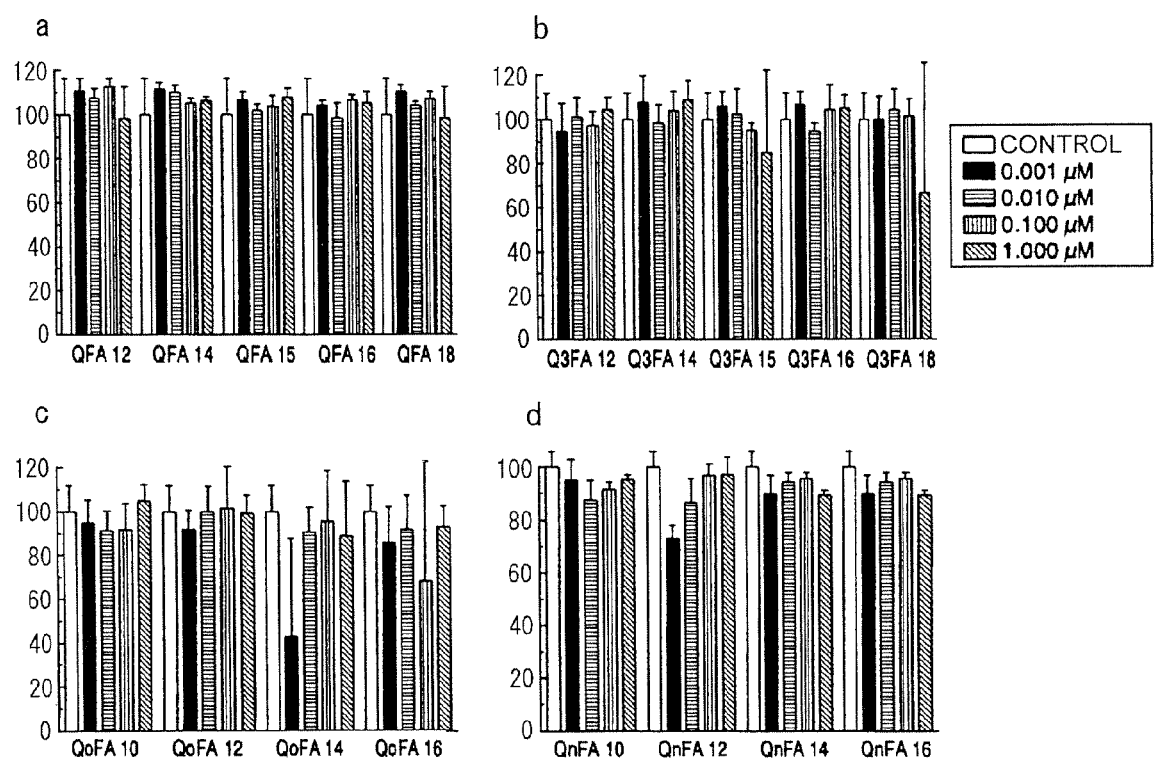
FIG. 1 shows graphs indicating the toxicity of QFAs to a cultured C6 cell line. The abbreviations refer to the following compounds:
QFA12: 12-(2,5-dimethoxyphenyl)dodecan-1-ol (5)
QFA 14: 14-(2,5-dimethoxyphenyl)tetradecan-1-ol (6)
QFA15: 15-(2,5-dimethoxyphenyl)pentadecan-1-ol (7)
QFA16: 16-(2,5-dimethoxyphenyl)hexadecan-1-ol (8)
QFA 18: 18-(2,5-dimethoxyphenyl)octadecan-1-ol (9)
Q3FA12: 12-((2,4,5)-trimethoxyphenyl)dodecan-1-ol (14)
Q3FA14: 14-((2,4,5)-trimethoxyphenyl)tetradecan-1-ol (13)
Q3FA15: 15-((2,4,5)-trimethoxyphenyl)pentadecan-1-ol (15)
Q3FA16: 16-((2,4,5)-trimethoxyphenyl)hexadecan-1-ol (16)
Q3FA18: 18-((2,4,5)-trimethoxyphenyl)octadecan-1-ol (17)
QoFA10: 10-(2,5-dimethoxyphenoxy)-decan-1-ol (28)
QoFA12: 12-(2,5-dimethoxyphenoxy)-dodecan-1-ol (29)
QoFA14: 14-(2,5-dimethoxyphenoxy)-tetradecan-1-ol (27)
QoFA16: 16-(2,5-dimethoxyphenoxy)-hexadecan-1-ol (30)
QnFA10: 10-(2,5-dimethoxyphenylamino)decan-1-ol (24)
QnFA 12: 12-(2,5-dimethoxyphenylamino)dodecan-1-ol (23)
QnFA14: 14-(2,5-dimethoxyphenylamino)tetradecan-1-ol (22)
QnFA16: 16-(2,5-dimethoxy-phenylamino)hexadecane-1-ol (21)

Compounds that are useful in the present invention are a series of compounds that can be referred to as the so-called hydroquinone long-chain derivatives and/or phenoxy long-chain derivatives, in particular, hydroquinone long-chain alcohol derivatives and/or phenoxy long-chain alcohol derivatives; and are compounds represented by formula (1) shown below:

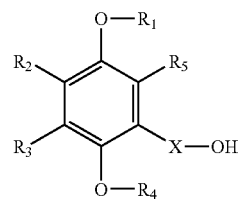

In formula (1) shown above, preferably, $R_1$, $R_2$, $R_3$, $R_4$, and $R_5$ are each individually selected from among a hydrogen atom, methyl group, acetyl group, hydroxyl group, and alkoxy group.

The alkyl group is preferably a C1-C6 alkyl group, and without particular limitation, examples include a methyl group, ethyl group, propyl group, butyl group, pentyl group, and hexyl group; and a methyl group is particularly preferred. Herein, "C1-Cn" means that the number of carbon atoms is one to n, and "C1-C6" means that the number of carbon atoms is one to six.

The alkoxy group is preferably a C1-C6 alkoxy group, and without particular limitation, examples include a methoxy group, ethoxy group, propoxy group, and butoxy group; and a methoxy group is particularly preferred. "C1-C6 alkoxy group" means an oxy group to which the above-defined "C1-n alkyl group" is bonded.

Without limitation, $R_1$, $R_2$, $R_3$, $R_4$, and $R_5$ are particularly preferably hydrogen atoms in the present invention.

Furthermore, preferably $R_1$, $R_3$, $R_4$, and $R_5$ are hydrogen atoms, and $R_2$ is an alkoxy group, in particular a methoxy group, but the present invention is not limited thereto.

X represents an alkylene group or an alkenylene group, and in particular, X is preferably an alkylene group or alkenylene group with 10 to 20 carbons, or more preferably 12 to 18 carbons, but the present invention is not limited thereto. Even more preferably, X is an alkylene group with 12 to 18 carbons.

Furthermore, hydroquinone long-chain derivative compounds represented by formula (2) shown below can be used as useful compounds in the present invention:

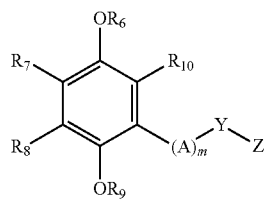

In formula (2) shown above, preferably, $R_6$, $R_7$, $R_8$, $R_9$, and $R_{10}$ are each individually selected from among a hydrogen atom, alkyl group, acetyl group, hydroxyl group, and alkoxy groups such as ethoxy group and methoxy group. Particularly preferably, $R_6$, $R_7$, $R_8$, $R_9$, and $R_{10}$ are hydrogen atoms, but the present invention is not limited thereto.

The alkyl group is preferably a C1-C6 alkyl group, and without particular limitation, examples include a methyl group, ethyl group, propyl group, butyl group, pentyl group, and hexyl group; and a methyl group is particularly preferred.

The alkoxy group is preferably a C1-C6 alkoxy group, and without particular limitation, examples include a methoxy group, ethoxy group, propoxy group, and butoxy group; and a methoxy group is particularly preferred.

Without limitation, $R_6$, $R_7$, $R_8$, $R_9$, and $R_{10}$ are particularly preferably hydrogen atoms in the present invention.

Furthermore, preferably $R_6$, $R_8$, $R_9$, and $R_{10}$ are hydrogen atoms, and $R_7$ is an alkoxy group, in particular a methoxy group, but the present invention is not limited thereto.

A represents an oxygen atom or NH, and m is 0 or 1.

Y represents an alkylene group or alkenylene group, and in particular, Y is preferably an alkylene group or alkenylene group with 10 to 20 carbons, or more preferably 12 to 18 carbons, but the present invention is not limited thereto. Y is even more preferably an alkylene group with 12 to 18 carbons.

Z represents a hydrogen atom or a hydroxyl group. Z is particularly preferably a hydroxyl group.

The structural formulas of the compounds described herein may represent certain isomers for convenience. However, the present invention comprises all isomers such as geometric isomers, stereoisomers, and tautomers that structurally arise from the compounds, and mixtures of isomers; and it is not limited to the isomers represented by the formulas shown for convenience, and may be any one or a mixture of isomers.

The compounds of the present invention can be obtained by methods such as the following:

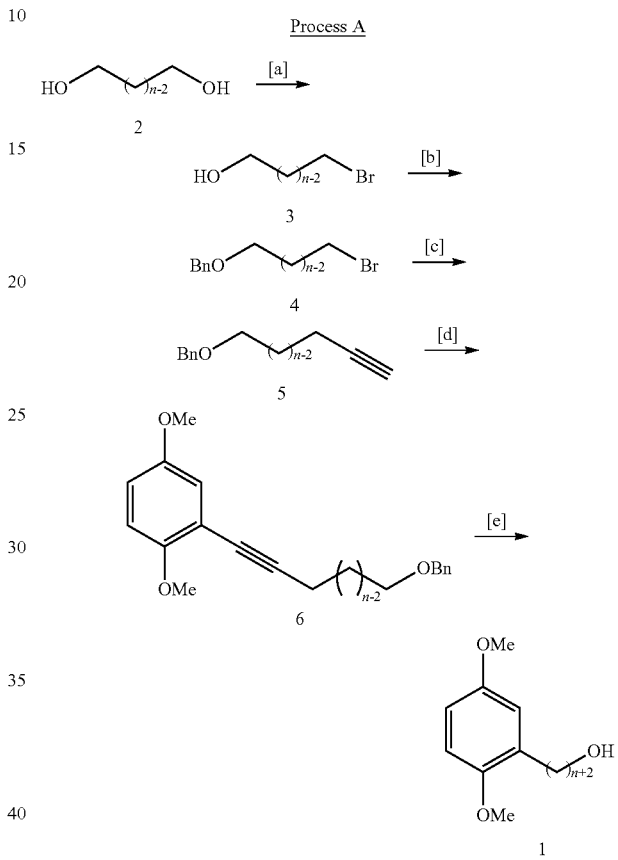

[a] HBr 57%, cyclohexane, reflux, 6 hours;
[b] 1) NaH, THF, RT, 30 minutes, 2) BnBr, THF, reflux, 24 hours;
[c] lithium acetylide diamine complex, DMSO, 0° C. to RT, 12 hours;
[d] 2, 5-dimethoxy-1-bromobenzene, Pd(PPh$_3$)$_4$, piperidine, 80° C., 6 hours;
[e] Pd/C5%, H$_2$, EtOH, one day Compound 1 of the present invention shown in Process A can be obtained by the following five steps:

diol 2 is reacted with hydrobromic acid (57%) in cyclohexane to obtain ω-bromoalkanol 3;

the obtained compound 3 is reacted with a strong base (NaH) and with benzyl bromide in tetrahydrofuran to obtain 1-((n-bromoalkyloxy)methyl)benzene 4;

the obtained compound 4 is reacted with a suspension of a complex of lithium acetylide and ethane-1,2-diamine in dimethylsulfoxide to obtain 1-((alk(n+2)ynyloxy)methyl)benzene 5;

the obtained compound 5 is reacted with 2,5-dimethoxy-1-bromobenzene in the presence of tetrakis(triphenylphosphine)palladium in piperidine to obtain 2-(n+2(benzyloxy)alk-1-ynyl)-1,4-dimethoxybenzene 6; and the obtained compound 6 was reacted under a stream of hydrogen in the presence of palladium-carbon to obtain n-(2,5-dimethoxyphenyl)alkan-1-ol 1.

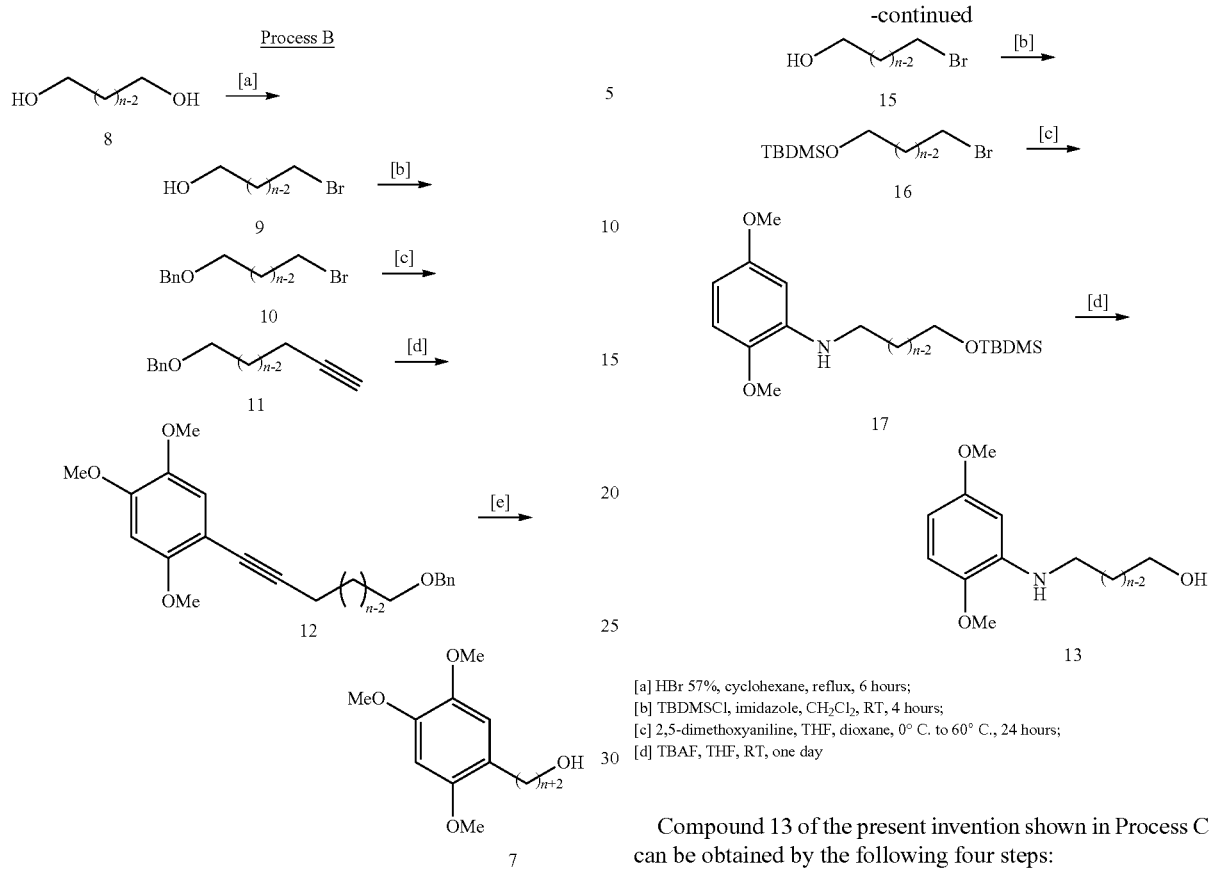

[a] HBr 57%, cyclohexane, reflux, 6 hours;
[b] 1) NaH, THF, RT, 30 minutes, 2) BnBr, THF, reflux, 24 hours;
[c] lithium acetylide diamine complex, DMSO, 0° C. to RT, 12 hours;
[d] 2,4,5-trimethoxy-1-bromobenzene, Pd(PPh$_3$)$_4$, piperidine, 80° C., 24 hours;
[e] Pd/C5%, H$_2$, EtOH, one day Compound 7 of the present invention shown in Process B can be obtained by the following five steps:

diol 8 is reacted with hydrobromic acid (57%) in cyclohexane to obtain ω-bromoalkanol 9;

the obtained compound 9 is reacted with a strong base (NaH) and with benzyl bromide in tetrahydrofuran to obtain 1-((n-bromoalkyloxy)methyl)benzene 10;

the obtained compound 10 is reacted with a suspension of a complex of lithium acetylide and ethane-1,2-diamine in dimethylsulfoxide to obtain 1-((alk(n+2)ynyloxy)methyl)benzene 11;

the obtained compound 11 is reacted with 2,4,5-trimethoxy-1-bromobenzene in the presence of tetrakis(triphenylphosphine)palladium in piperidine to obtain 2-(n+2(benzyloxy)alk-1-ynyl)-1,4,5-trimethoxybenzene 12; and the obtained compound 12 was reacted under a stream of hydrogen in the presence of palladium-carbon to obtain n-(2,4,5-trimethoxyphenyl)alkan-1-ol 7.

Process C

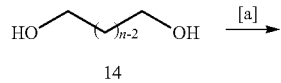

[a] HBr 57%, cyclohexane, reflux, 6 hours;
[b] TBDMSCl, imidazole, CH$_2$Cl$_2$, RT, 4 hours;
[c] 2,5-dimethoxyaniline, THF, dioxane, 0° C. to 60° C., 24 hours;
[d] TBAF, THF, RT, one day Compound 13 of the present invention shown in Process C can be obtained by the following four steps:

diol 14 is reacted with hydrobromic acid (57%) in cyclohexane to obtain ω-bromoalkanol 15;

the obtained compound 15 is reacted with t-butyldimethylsilylchloride and imidazole in dichloromethane to obtain (n-bromoalkyloxy)(t-butyl)dimethylsilane 16;

the obtained compound 16 is reacted with 2,5-dimethoxyaniline in tetrahydrofuran, n-butyl lithium, and dioxane to obtain N-(n-(t-butyldimethylsilyloxy)alkyl-2,5-dimethoxybenzenamine 17; and the obtained compound 17 is reacted with tetrabutylammonium fluoride (1M) in THF to obtain n-(2,5-dimethoxyphenylamino)alkan-1-ol 13.

Process D

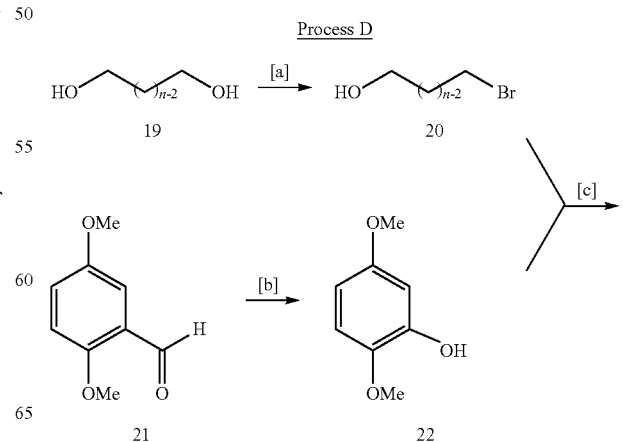

-continued

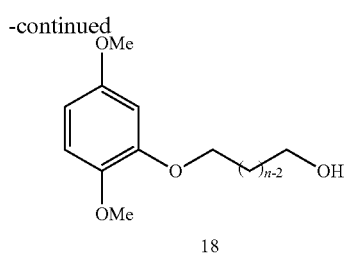

18

[a] HBr 57%, cyclohexane, reflux, 6 hours;
[b] 1) mCPBA, CH$_2$Cl$_2$, 24 hours, 2) NaOH 10%;
[c] 2,5-dimethoxyphenol, acetone, reflux, 24 hours Compound 18 of the present invention shown in Process D can be obtained by the following three steps:

diol 19 is reacted with hydrobromic acid (57%) in cyclohexane to obtain ω-bromoalkanol 20;

the obtained compound 20 is reacted with 2,5-dimethoxyphenol 22 and potassium carbonate in acetone to obtain n-(2,5-dimethoxyphenoxy)alkan-1-ol 18; and compound 22 can be obtained by reacting 2,5-dimethoxybenzaldehyde with m-chloroperbenzoic acid (mCPBA) in dichloromethane, and then performing an in situ saponification in an aqueous 10% sodium hydroxide solution.

Without limitation, examples of excipients include lactose, cornstarch, sucrose, glucose, sorbitol, and crystalline cellulose.

Without limitation, examples of binders include polyvinyl alcohol, polyvinyl ether, ethylcellulose/methylcellulose, gum arabic, tragacanth, gelatin, shellac, hydroxypropylcellulose, hydroxypropyl starch, and polyvinylpyrrolidone.

Without limitation, examples of disintegrators include starch, agar, gelatin powder, crystalline cellulose, calcium carbonate, sodium hydrogen carbonate, calcium citrate, dextran, and pectin.

Without limitation, examples of lubricants include magnesium stearate, talc, polyethylene glycols, silica, and hardened vegetable oils.

Coloring agents are not particularly limited so long as they are approved for addition to pharmaceuticals.

Without limitation, examples of flavoring agents include cocoa powder, menthol, aromatic acid, mint oil, borneol, and cinnamon powder.

Without limitation, examples of diluents include sterilized distilled water, deionized water, physiological saline, and aqueous solutions of glucose, mannitol, lactose, or such.

Since the compounds of the present invention are low-molecular weight, pharmaceuticals thereof can be administered orally or parenterally (intramuscularly, subcutaneously, intravenously, as suppositories, transdermally, or such). The

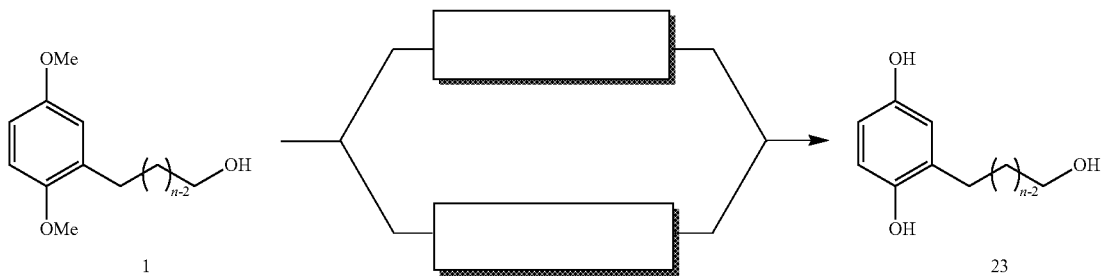

Process E

Compound 23 of the present invention shown in Process E can be obtained in one step, in which compound 1 is reacted with boron tribromide in dichloromethane.

Treatments such as methods for synthesis and methods for purification of the above-described compounds of the present invention are not limited to those described above, and treatments such as methods for synthesis and methods for purification ordinarily used in the art can be applied. The compounds of the present invention may be in the form of pharmaceutically acceptable salts, or solvates or hydrates thereof.

Since the compounds of the present invention have antioxidative activity or nerve growth-promoting activity, they are useful as preventive and/or therapeutic agents for neuropathic diseases in which the neural network is destroyed due to damage or degeneration of neurons.

One or two or more of the compounds of the present invention can be used as pharmaceutical compositions in combination with various types of pharmaceutically acceptable adjuvants. For example, when preparing oral preparations, addition of excipients, and if necessary, binders, disintegrators, lubricants, coloring agents, flavoring agents, or such is followed by dilution with diluents and such as necessary to produce tablets, coated tablets, granules, capsules, solutions, syrups, elixirs, oil-based or water-based emulsions by standard methods.

dose of a pharmaceutical comprising a compound of the present invention as an active ingredient can be determined appropriately by considering various factors such as administration route, and the age, weight, symptoms and such of the subject animal including humans. The daily dose for oral administration is 0.01 to 1,000 mg, or preferably 1 to 100 mg. The daily dose for parenteral administration is 0.01 to 1,000 mg, or preferably 1 to 100 mg.

All prior art references cited herein are incorporated herein by reference.

EXAMPLES

Synthesis Examples

Hereinbelow, the present invention will be described with reference to Synthesis Examples A-(1) to E-(34), but it is not to be construed as being limited thereto.

Synthesis Example A-(1)

1,10-Decanediol (4 g) was dissolved in 100 ml of cyclohexane, and 57% aqueous hydrobromic acid solution (58 ml) was added to this solution. The reaction mixture was refluxed for six hours while stirring. After the reaction, the mixture was extracted three times with diethyl ether. The organic layer was neutralized with saturated sodium hydrogen carbonate solution, washed with saline solution, dried over magnesium sulfate, and filtered, and the solvent was distilled off under reduced pressure. Purification of the residue by silica gel flash chromatography (hexane:ethyl acetate=7:3) gave 10-bromo-decan-1-ol as white crystals at an 89% yield.

Molecular weight: 237.18 ($C_{10}H_{21}BrO$)

TLC: (hexane-ethyl acetate=7-3) Rf value: 0.53

$^1$H-NMR: (300 MHz, CDCl$_3$) δ: 1.26 (s large, 12H, —(CH$_2$)$_6$—); 1.56 (qt, 2H, J=7.0 Hz, —CH$_2$—); 1.85 (qt, 2H, J=7.1 Hz, —CH$_2$—); 3.40 (t, 2H, J=6.9 Hz, —CH$_2$—Br); 3.64 (t, 2H, J=6.6 Hz, —CH$_2$—O—)

$^{13}$C-NMR: (75 MHz, CDCl$_3$) δ: 25.70; 28.14-29.45; 32.77; 32.80; 34.03; 63.05

Synthesis Example A-(2)

10-Bromodecan-1-ol (4.6 g) was dissolved in 20 ml of dried THF, and sodium hydride (933.6 mg) was added to this solution. The reaction mixture was stirred at room temperature for 30 minutes, then benzyl bromide (2.78 ml) was added using a syringe, and the reaction mixture was refluxed for 24 hours while stirring. Saturated ammonium chloride solution was added to the reaction mixture, which was then extracted with diethyl ether. The organic layer was washed with saline solution, dried over magnesium sulfate, and filtered, and the solvent was distilled off under reduced pressure. Purification of the residue by silica gel flash chromatography (hexane:dichloromethane=8:2) gave 1-((10-bromodecanoxy)methyl)benzene as a colorless oil at an 88% yield.

Molecular weight: 327.30 ($C_{17}H_{27}BrO$)

TLC: (hexane-dichloromethane 8-2) Rf value=0.44

$^1$H-NMR: (300 MHz, CDCl$_3$) δ: 1.26 (s large, 12H, —(CH$_2$)$_6$—); 1.58 (qt, 2H, J=7.3 Hz, —CH$_2$—); 1.85 (qt, 2H, J=7.1 Hz, —CH$_2$—); 3.40 (t, 2H, J=7.1 Hz, —CH$_2$—Br); 3,46 (t, 2H, J=6.6 Hz, —CH$_2$—O—); 4.50 (s, 2H, —O—CH$_2$-Ph); 7.35 (m, 5H, -Ph)

$^{13}$C-NMR: (75 MHz, CDCl$_3$) δ: 26.17; 28.16-30.75; 32.83; 34.05; 70.50; 72.86; 127.46; 127.61; 128.33; 129.86; 138.71

Synthesis Example A-(3)

A solution of 1-((10-bromodecanoxy)methyl)benzene (5.52 g) in DMSO (8 ml) was added drop-wise to a suspension of a complex of lithium acetylide and ethane-1,2-diamine (2.33 g) in DMSO (11 ml), at 0° C. The reaction mixture was stirred at 0° C. for 30 minutes, and then left to stand at room temperature for 12 hours. Saturated potassium chloride solution was added to the reaction mixture, which was then extracted three times with hexane. The organic layer was washed with saline solution, dried over magnesium sulfate, and filtered, and the solvent was distilled off under reduced pressure. Purification of the residue by silica gel flash chromatography (hexane:dichloromethane=7:3) gave 1-((dodec (12)ynyloxy)methyl)benzene as a colorless oil at a 76% yield.

Molecular weight: 272.43 ($C_{19}H_{28}O$)

TLC: (hexane-dichloromethane 7-3) Rf value=0.30

$^1$H-NMR: (300 MHz, CDCl$_3$) δ: 1.28 (s large, 12H, —(CH$_2$)$_6$—); 1.52 (qt, 2H, J=7.3 Hz, —CH$_2$—); 1.61 (qt, 2H, J=7.0 Hz, —CH$_2$—); 1.94 (t, 1H, J=2.5 Hz, —C—CH); 2.18 (td, 2H, J$^3$=6.9 Hz, J$^4$=2.4 Hz, —CH$_2$—C≡C—); 3.46 (t, 2H, J=6.8 Hz, —CH$_2$—O—); 4,50 (s, 2H, —O—CH$_2$-Ph); 7, 33 (m, 5H, -Ph)

$^{13}$C-NMR: (75 MHz, CDCl$_3$) δ: 18.39; 26.18, 28.48; 28.74; 29.08; 29.44; 29.52; 29.76; 35.76; 68.03; 70.51; 72.85; 84.81; 127.46; 127.61; 128.35; 138.71

Synthesis Example A-(4)

2,5-Dimethoxy-1-bromobenzene (434.12 mg) and tetrakis(triphenylphosphine)palladium (Pd(PPh$_3$)$_4$) (161.8 mg) were dissolved in 3 ml of piperidine, and a solution of 1-((dodec (12)ynyloxy)methyl)benzene) (1.1 g) in 3 ml of piperidine was added to this solution. The reaction mixture was stirred at 80° C. for six hours. Saturated ammonium chloride solution was added to the reaction mixture, which was then extracted three times with diethyl ether. The organic layer was washed with saline solution, dried over magnesium sulfate, and filtered, and the solvent was distilled off at reduced pressure. Purification of the residue by silica gel chromatography (hexane:ethyl acetate=95:5) gave 2-(12(benzyloxy)dodec-1-ynyl)-1,4-dimethoxybenzene as a colorless oil at a 71% yield.

Molecular weight: 408.57 ($C_{27}H_{36}O_3$)

TLC: (hexane-ethyl acetate 95-5) Rf value=0.2

$^1$H-NMR: (300 MHz, CDCl$_3$) δ: 1.26 (s large, 12H, —(CH$_2$)$_6$—); 1.42 (qt, 2H, J=7.2 Hz, —CH$_2$—); 1.62 (qt, 2H, J=7.1 Hz, —CH$_2$—); 2.45 (t, 2H, J=6.9 Hz, —CH$_2$—C≡C); 3.46 (t, 2H, J=6.8 Hz, —O—CH$_2$—); 3.75 (s, 3H, —OCH$_3$); 3.83 (s, 3H, —OCH$_3$); 4.50 (s, 2H, —O—CH$_2$-Ph); 6.77 (s, 1H, aromatic-CH); 6.78 (d, 1H, J=1.5 Hz, aromatic-CH); 6.92 (dd, 1H, J$^3$=2.1 Hz, J$^5$=1.2 Hz, aromatic-CH); 7.33 (m, 5H, -Ph)

$^{13}$C-NMR: (75 MHz; CDCl$_3$) δ: 19.77; 26.19; 28.81; 28.95; 29.16; 29.48; 29.55; 29.77; 55.75; 55.45; 70.52; 72.85; 82.25; 94.79; 111.91; 113.76; 114.64; 118.44; 127.45; 127.61; 128.33; 138.72; 153.18; 154.33

Synthesis Example A-(5)

554.1 mg of 2-(12(benzyloxy)dodec-1-ynyl)-1,4-dimethoxybenzene was dissolved in 3 ml of ethanol, 5% palladium-carbon (60 mg) was added to this solution, and this was placed under hydrogen atmosphere. The reaction mixture was stirred for one day at room temperature. The reaction solution was filtered through Celite, and the solvent was distilled off at reduced pressure. Purification of the residue by silica gel chromatography (hexane:ethyl acetate=6:4) gave 12-(2,5-dimethoxyphenyl)dodecan-1-ol as a colorless oil at a 92% yield.

Molecular weight: 322.48 ($C_{20}H_{34}O_3$)

TLC: (hexane-ethyl acetate 6-4) Rf value=0.23

$^1$H-NMR: (300 MHz, CDCl$_3$) δ: 1.26 (s large, 16H, —(CH$_2$)$_8$—); 1.56 (qt, 4H, J=6.9 Hz, —CH$_2$—); 2.57 (t, 2H, J=7.7 Hz, —CH$_2$-Ph); 3.64 (t, 2H, J=6.6 Hz, —CH$_2$—O—); 3.76 (s, 3H, —OCH$_3$); 3.77 (s, 3H, —OCH$_3$); 6.67 (dd, 1H, J$^3$=8.7 Hz, J$^5$=3.0 Hz, aromatic-CH); 6.72 (d, 1H, J$^5$=3.0 Hz, aromatic-CH); 6.76 (d, 1H, J$^3$=8.7 Hz, aromatic-CH)

$^{13}$C-NMR: (75 MHz, CDCl$_3$) δ: 25.73; 29.42-30.32; 32.81; 55.65; 55.99; 63.10; 110.48; 111.19; 116.22; 132.71; 141.86; 151.77; 153.40.

Synthesis Example A-(6)

The compound, 14-(2,5-dimethoxyphenyl)tetradecan-1-ol, was obtained by a method similar to Synthesis Example A-(5).

Molecular weight: 350.54 ($C_{22}H_{38}O_3$)

TLC: (hexane-ethyl acetate 8-2) Rf value=0.48

$^1$H-NMR: (300 MHz, CDCl$_3$) δ: 1.26 (s large, 20H, —(CH$_2$)$_{10}$—); 1.56 (qt, 4H, J=6.8 Hz, —CH$_2$—); 2.57 (t, 2H, J=7.7 Hz, —CH$_2$-Ph); 3.63 (t, 2H, J=6.7 Hz, —CH$_2$—O—); 3.76 (s, 3H, —OCH$_3$); 3.77 (s, 3H, —OCH$_3$); 6.67 (dd, 1H, J$^3$=8.7 Hz, J$^5$=3.0 Hz, aromatic-CH); 6.72 (d, 1H, J$^5$=3.0 Hz, aromatic-CH); 6.77 (d, 1H, J$^3$=8.7 Hz, aromatic-CH)

$^{13}$C-NMR: (75 MHz, CDCl$_3$) δ: 25.73; 29.42-29.87; 32.23; 32.81; 55.65; 55.99; 63.09; 110.49; 111.20; 116.22; 132.72; 151.78; 153.41

Synthesis Example A-(7)

The compound, 15-(2,5-dimethoxyphenyl)pentadecan-1-ol, was obtained by a method similar to Synthesis Example A-(5).

Molecular weight: 364.56 (C$_{23}$H$_{40}$O$_3$)

TLC: (hexane-ethyl acetate 8-2) Rf value=0.4

$^1$H-NMR: (300 MHz, CDCl$_3$) δ: 1.26 (s large, 22H, —(CH$_2$)$_{11}$—); 1.56 (qt, 4H, J=6.8 Hz, —CH$_2$—); 2.56 (t, 2H, J=7.8 Hz, —CH$_2$-Ph); 3.63 (t, 2H, J=6.5 Hz, —CH$_2$—O—); 3.76 (s, 3H, —OCH$_3$); 3.77 (s, 3H, —OCH$_3$); 6.67 (dd, 1H, J$^3$=8.7 Hz, J$^5$=3.0 Hz, aromatic-CH); 6.72 (d, 1H, J$^5$=3.0 Hz, aromatic-CH); 6.76 (d, 1H, J$^3$=8.7 Hz, aromatic-CH)

$^{13}$C-NMR: (75 MHz, CDCl$_3$) δ: 25.73; 29.42-29.87; 30.23; 32.81; 55.65; 55.98; 63.10; 110.49; 111.20; 116.22; 132.73; 151.78; 153.41

Synthesis Example A-(8)

The compound, 16-(2,5-dimethoxyphenyl)hexadecan-1-ol, was obtained by a method similar to Synthesis Example A-(5).

Molecular weight: 378.59 (C$_{24}$H$_{42}$O$_3$)

TLC: (hexane-ethyl acetate 8-2) Rf value=0.28

$^1$H-NMR: (300 MHz, CDCl$_3$) δ: 1.25 (s large, 24H, —(CH$_2$)$_{12}$—); 1.56 (qt, 4H, J=6.8 Hz, —CH$_2$—); 2.57 (t, 2H, J=7.7 Hz, —CH$_2$-Ph); 3.63 (t, 2H, J=6.7 Hz, —CH$_2$—O—); 3.76 (s, 3H, —OCH$_3$); 3.77 (s, 3H, —OCH$_3$); 6.67 (dd, 1H, J$^3$=8.7 Hz, J$^5$=3.0 Hz, aromatic-CH); 6.72 (d, 1H, J$^5$=3.0 Hz, aromatic-CH); 6.76 (d, 1H, J$^3$=8.7 Hz, aromatic-CH)

$^{13}$C-NMR: (75 MHz, CDCl$_3$) δ: 25.73; 29.43-29.87; 30.23; 32.81; 55.65; 55.99; 63.10; 110.50; 111.20; 116.22; 132.73; 151.79; 153.41

Synthesis Example A-(9)

The compound, 18-(2,5-dimethoxyphenyl)octadecan-1-ol, was obtained by a method similar to Synthesis Example A-(5).

Molecular weight: 406.64 (C$_{26}$H$_{46}$O$_3$)

TLC: (hexane-ethyl acetate 6-4) Rf value=0.53

$^1$H-NMR: (300 MHz, CDCl$_3$) δ: 1.25 (s large, 28H, —(CH$_2$)$_{14}$—); 1.56 (qt, 4H, J=6.9 Hz, —CH$_2$—); 2.56 (t, 2H, J=7.7 Hz, —CH$_2$-Ph); 3.63 (t, 2H, J=6.6 Hz, —CH$_2$—O—); 3.76 (s, 3H, —OCH$_3$); 3.77 (s, 3H, —OCH$_3$); 6.67 (dd, 1H, J$^3$=8.7 Hz, J$^5$=3.0 Hz, aromatic-CH); 6.72 (d, 1H, J$^5$=3.0 Hz, aromatic-CH); 6.76 (d, 1H, J$^3$=8.7 Hz, aromatic-CH)

$^{13}$C-NMR: (75 MHz, CDCl$_3$) δ: 25.73; 29.43-29.88; 30.24; 32.81; 55.65; 55.98; 63.09; 110.45; 111.18; 116.21; 132.72; 151.77; 153.40

Synthesis Example B-(10)

1,10-Dodecanediol (2 g) was dissolved in 25 ml of cyclohexane, and 57% hydrobromic acid solution (25 ml) was added to this solution. The reaction mixture was refluxed for six hours while stirring. After the reaction, the mixture was extracted three times with diethyl ether. The organic layer was neutralized with saturated sodium hydrogen carbonate solution, washed with saline solution, dried over magnesium sulfate, and filtered, and the solvent was distilled off under reduced pressure. Purification of the residue by silica gel flash chromatography (hexane:ethyl acetate=7:3) gave 12-bromododecan-1-ol as white crystals at a 73% yield.

Molecular weight: 265.23 (C$_{12}$H$_{25}$BrO)

TLC: (hexane-ethyl acetate 7-3) Rf value=0.53

$^1$H-NMR: (300 MHz, CDCl$_3$) δ: 1.26 (s large, 16H, —(CH$_2$)$_6$—); 1.56 (qt, 2H, J=6.9 Hz, —CH$_2$—); 1.85 (qt, 2H, J=7.1 Hz, —CH$_2$—); 3.40 (t, 2H, J=7.1 Hz, —CH$_2$—Br); 3.64 (t, 2H, J=6.6 Hz, —CH$_2$—O—)

$^{13}$C-NMR: (75 MHz; CDCl$_3$) δ: 25.72; 27.28; 28.16; 28.74; 29.40; 29.49; 29.55; 30.92; 32.79; 32.82; 34.05; 63.08

Synthesis Example B-(11)

12-Bromododecan-1-ol (1.83 g) was dissolved in 7 ml of dried THF, and sodium hydride (331.2 mg) was added to this solution. The reaction mixture was stirred at room temperature for 30 minutes, then benzyl bromide (0.99 ml) was added using a syringe, and the reaction mixture was refluxed for 24 hours while stirring. Saturated ammonium chloride solution was added to the reaction mixture, which was then extracted with diethyl ether. The organic layer was washed with saline solution, dried over magnesium sulfate, and filtered, and the solvent was distilled off under reduced pressure. Purification of the residue by silica gel flash chromatography (hexane:dichloromethane=8:2) gave 1-((12-bromododecanoxy)methyl)benzene as a colorless oil at a 73% yield.

Molecular weight: 355.35 (C$_{19}$H$_{31}$BrO)

TLC: (hexane-dichloromethane 8-2) Rf value=0.44

$^1$H-NMR: (300 MHz, CDCl$_3$) δ: 1.26 (s large, 12H, —(CH$_2$)$_6$—); 1.58 (qt, 2H, J=7.3 Hz, —CH$_2$—); 1.85 (qt, 2H, J=7.1 Hz, —CH$_2$—); 3.40 (t, 2H, J=7.1 Hz, —CH$_2$—Br); 3.46 (t, 2H, J=6.6 Hz, —CH$_2$—O—); 4.50 (s, 2H, —O—CH$_2$-Ph); 7.35 (m, 5H, -Ph)

$^{13}$C-NMR: (75 MHz, CDCl$_3$) δ: 26.18; 28.17; 28.76; 29.38; 29.42; 29.47; 29.51; 29.77; 32.84; 34.05; 69.64; 72.85; 122.01; 127.44; 127.61; 127.78; 128.33; 134.97; 138.72

Synthesis Example B-(12)

A solution of 1-((12-bromododecanoxy)methyl)benzene (1.75 g) in DMSO (2.3 ml) was added drop-wise to a suspension of a complex of lithium acetylide and ethane-1,2-diamine (681.32 mg) in DMSO (3.3 ml), at 0° C. The reaction mixture was stirred at 0° C. for 30 minutes, and then left to stand at room temperature for 12 hours. Saturated potassium chloride solution was added to the reaction mixture, which was then extracted three times with hexane. The organic layer was washed with saline solution, dried over magnesium sulfate, and filtered, and the solvent was distilled off under reduced pressure. Purification of the residue by silica gel flash chromatography (hexane:dichloromethane=7:3) gave 1-((tetradec(14)ynyloxy)methyl)benzene) as a colorless oil at a 76% yield.

Molecular weight: 300.48 (C$_{21}$H$_{32}$O)

TLC: (hexane-dichloromethane 7-3) Rf value=0.30

$^1$H-NMR: (300 MHz, CDCl$_3$) δ: 1.28 (s large, 16H, —(CH$_2$)$_8$—); 1.61 (qt, 4H, J=7.0 Hz, —CH$_2$—); 1.94 (t, 1H, J=2.7 Hz, ≡CH); 2, 18 (td, 2H, J$^3$=7.2 Hz, J$^4$=2.7 Hz, —CH—C≡); 3.46 (t, 2H, J=6.6 Hz, —CH$_2$—O—); 4.50 (s, 2H, —O—CH$_2$-Ph); 7.33 (m, 5H, -Ph)

$^{13}$C-NMR: (75 MHz, CDCl$_3$) δ: 18.39; 26.18; 28.49-29.56; 29.77; 68.01; 70.53; 72.85; 84.81; 127.44; 127.61; 127.77; 128.32; 128.33; 138.73

Synthesis Example B-(13)

2,4,5-Trimethoxy-1-bromobenzene (411.16 mg) and tetrakis(triphenylphosphine)palladium (Pd(PPh$_3$)$_4$) (135.2 mg) were dissolved in 2.5 ml of piperidine, and a solution of 1-((tetradec(14)ynyloxy)methyl)benzene) (1 g) in 2.5 ml of piperidine was added to this solution. The reaction mixture was stirred at 80° C. for 24 hours. Saturated ammonium chloride solution was added to the reaction mixture, which was then extracted three times with diethyl ether. The organic layer was washed with saline solution, dried over magnesium sulfate, and filtered, and the solvent was distilled off at reduced pressure. Purification of the residue by silica gel chromatography (hexane:ethyl acetate=75:25) gave 2-(14(bezyloxy)tetradec-1-ynyl)-1,2,4-trimethoxybenzene as a mixture with residual 2,4,5-trimethoxy-1-bromobenzene.

The obtained residue (612.8 mg) was dissolved in 2.6 ml of ethanol, 5% palladium-carbon (62 mg) was added to this solution, and this was placed under hydrogen atmosphere. The reaction mixture was stirred for one day at room temperature. The reaction solution was filtered through Celite, and the solvent was distilled off at reduced pressure. Purification of the residue by silica gel chromatography (hexane:ethyl acetate=6:4) gave 14-(2,4,5-trimethoxyphenyl)tetradecan-1-ol as white crystals at a 74% yield.

Molecular weight: 380.56 (C$_{23}$H$_{40}$O$_4$)
TLC: (hexane-ethyl acetate 75-25) Rf value=0.15
$^1$H-NMR: (300 MHz, CDCl$_3$) δ: 1.26 (s large, 20H, —(CH$_2$)$_{10}$—); 1.56 (qt, 4H, J=6.8 Hz, —CH$_2$—); 2.56 (t, 2H, J=7.7 Hz, —CH$_2$-Ph); 3.63 (t, 2H, J=6.6 Hz, —CH$_2$—O—); 3.79 (s, 3H, —OCH$_3$); 3.83 (s, 3H, —OCH$_3$); 3.87 (s, 3H, —OCH$_3$); 6.52 (s, 1H, aromatic-CH); 6.68 (s, 1H, aromatic-CH)
$^{13}$C-NMR: (75 MHz, CDCl$_3$) δ: 25.73; 29.42-30.39; 31,88; 32.81; 56.24; 56.51; 56.66; 63.70; 98.02; 114.13; 123.07; 142.81; 147.43; 151.44

Synthesis Example B-(14)

The compound, 12-(2,4,5-trimethoxyphenyl)dodecan-1-ol, was obtained by a method similar to Synthesis Example B-(13).

Molecular weight: 352.51 (C$_{21}$H$_{36}$O$_4$)
TLC: (hexane-ethyl acetate 6-4) Rf value=0.37
$^1$H-NMR: (300 MHz, CDCl$_3$) δ: 1.26 (s large, 16H, —(CH$_2$)$_8$—); 1.56 (qt, 4H, J=7.1 Hz, —CH$_2$—); 2.53 (t, 2H, J=7.7 Hz, —CH$_2$-Ph); 3.63 (t, 2H, J=6.4 Hz, —CH$_2$—O—); 3.79 (s, 3H, —OCH$_3$); 3.83 (s, 3H, —OCH$_3$); 3.87 (s, 3H, —OCH$_3$); 6.51 (s, 1H, aromatic-CH); 6.87 (s, 1H, aromatic-CH)
$^{13}$C-NMR: (75 MHz, CDCl$_3$) δ: 25.73; 29.42-29.63; 30.39; 32.80; 56.24; 56.51; 56.67; 63.09; 98.02; 114.13; 123.07; 142.81; 147.43; 151.45

Synthesis Example B-(15)

The compound, 15-(2,4,5-trimethoxyphenyl)pentadecan-1-ol, was obtained by a method similar to Synthesis Example B-(13).

Molecular weight: 394.59 (C$_{24}$H$_{42}$O$_4$)
TLC: (hexane-ethyl acetate 6-4) Rf value=0.34
$^1$H-NMR: (300 MHz, CDCl$_3$) δ: 1.26 (s large, 22H, —(CH$_2$)$_{11}$—); 1.56 (qt, 4H, J=7.1 Hz, —CH$_2$—); 2.53 (t, 2H, J=7.6 Hz, —CH$_2$-Ph); 3.63 (t, 2H, J=6.6 Hz, —CH$_2$—O—); 3.79 (s, 3H, —OCH$_3$); 3.83 (s, 3H, —OCH$_3$); 3.87 (s, 3H, —OCH$_3$); 6.51 (s, 1H, aromatic-CH); 6.68 (s, 1H, aromatic-CH)
$^{13}$C-NMR: (75 MHz, CDCl$_3$) δ: 25.73; 29.43-29.66; 30.39; 32.81; 56.24; 55.51; 56.67; 63.71; 98.02; 114.12; 123.07; 142.81; 147.43; 151.44

Synthesis Example B-(16)

The compound, 16-(2,4,5-trimethoxyphenyl)hexadecan-1-ol, was obtained by a method similar to Synthesis Example B-(13).

Molecular weight: 408.61 (C$_{25}$H$_{44}$O$_4$)
TLC: (hexane-ethyl acetate 6-4) Rf value=0.34
$^1$H-NMR: (300 MHz, CDCl$_3$) δ: 1.21 (s large, 24H, —(CH$_2$)$_{12}$—); 1.52 (qt, 4H, J=6.6 Hz, —CH$_2$—); 2.48 (t, 2H, J=7.7 Hz, —CH$_2$-Ph); 3.59 (t, 2H, J=6.6 Hz, —CH$_2$—O—); 3.75 (s, 3H, —OCH$_3$); 3.79 (s, 3H, —OCH$_3$); 3.83 (s, 3H, —OCH$_3$); 6.51 (s, 1H, aromatic-CH); 6.68 (s, 1H, aromatic-CH)
$^{13}$C-NMR: (75 MHz, CDCl$_3$) δ: 25.73; 29.43-30.97; 31.87; 32.81; 56.24; 56.51; 56.66; 63.11; 98.02; 114.12; 123.08; 142.81; 147.43; 151.44

Synthesis Example B-(17)

The compound, 18-(2,4,5-trimethoxyphenyl)octadecan-1-ol, was obtained by a method similar to Synthesis Example B-(13).

Molecular weight: 436.67 (C$_{27}$H$_{48}$O$_4$)
TLC: (hexane-ethyl acetate 6-4) Rf value=0.45
$^1$H-NMR: (300 MHz, CDCl$_3$) δ: 1.25 (s large, 28H, —(CH$_2$)$_{14}$—) 1.54 (qt, 4H, J=6.8 Hz, —CH$_2$—); 2.53 (t, 2H, J=7.7 Hz, —CH$_2$-Ph); 3.63 (t, 2H, J=6.6 Hz, —CH$_2$—O—); 3.79 (s, 3H, —OCH$_3$); 3.83 (s, 3H, —OCH$_3$); 3.87 (s, 3H, —OCH$_3$); 6.51 (s, 1H, aromatic-CH); 6.69 (s, 1H, aromatic-CH)
$^{13}$C-NMR: (75 MHz, CDCl$_3$) δ: 25.73; 29.43-29.69; 30.39; 32.81; 56.24; 56.50; 56.66; 63.10; 98.02; 114.12; 123.08; 142.81; 147.42; 151.44

Synthesis Example C-(18)

1,16-Hexadecanediol (13.75 g) was dissolved in 37 ml of cyclohexane, and 57% hydrobromic acid solution (37 ml) was added to this solution. The reaction mixture was refluxed for six hours while stirring. After the reaction, the mixture was extracted three times with diethyl ether. The organic layer was neutralized with saturated sodium hydrogen carbonate solution, washed with saline solution, dried over magnesium sulfate, and filtered, and the solvent was distilled off under reduced pressure. Purification of the residue by silica gel flash chromatography (hexane:ethyl acetate=7:3) gave 16-bromohexadecan-1-ol as white crystals at a 67% yield.

Molecular weight: 320.9 (C$_{16}$H$_{33}$BrO)
TLC: (hexane-ethyl acetate 7-3) Rf value=0.53
$^1$H-NMR: (300 MHz, CDCl$_3$) δ: 1.26 (s large, 24H, —(CH$_2$)$_{12}$—); 1.56 (qt, 2H, J=7.2 Hz, —CH$_2$—); 1.85 (qt, 2H, J=7.1 Hz, —CH$_2$—); 3.40 (t, 2H, J=7.1 Hz, —CH$_2$—Br); 3.63 (t, 2H, J=6.6 Hz, —CH$_2$—O—)
$^{13}$C-NMR: (75 MHz, CDCl$_3$) δ: 25.84; 27.28; 28.22; 29.48-29.50; 32.90; 33.20; 34.01; 63.01

Synthesis Example C-(19)

16-Bromohexadecan-1-ol (1 g) was dissolved in 20 ml of dichloromethane, and imidazole (317.9 mg) and t-butyldimethylsilyl chloride (701.4 mg) were added to this solution. The reaction mixture was stirred at room temperature for four hours. Saturated ammonium chloride solution was added to the reaction mixture, which was then extracted three times with dichloromethane. The organic layer was washed with saline solution and dried over magnesium sulfate, and the solvent was distilled off under reduced pressure. Purification of the residue by silica gel flash chromatography (heptane: ethyl acetate=7:3) gave (16-bromohexadecyloxy)-t-butyldimethylsilane as a colorless oil at an 81% yield.

Molecular weight: 435.13 ($C_{22}H_{47}BrOSi$)
TLC: (hexane-ethyl acetate 7-3) Rf value=0.95
$^1$H-NMR: (300 MHz, CDCl$_3$) δ: 0.01 (s, 6H, —Si—(CH$_3$)$_2$); 0.86 (s, 9H, —Si-tBu); 1.23 (s large, 24H, —(CH$_2$)$_{12}$—); 1.40 (m, 2H, —CH$_2$—); 1.75 (qt, 2H. J=7.1 Hz, —CH$_2$—); 3.33 (t, 2H, J=6.9 Hz, —CH$_2$—Br); 3.52 (t, 2H, J=6.6 Hz, —CH$_2$—O—)
$^{13}$C-NMR: (75 MHz, CDCl$_3$) δ: −5.20; 18.36; 25.63; 25.77; 25.97; 28.16-29.46; 32.83; 32.85; 33.97; 63.28

Synthesis Example C-(20)

2,5-Dimethoxyaniline (352.3 mg) was dissolved in 20 ml of tetrahydrofuran, and then 2.3 ml of n-butyl lithium (1.0 M solution in hexane), 3 ml of a solution of (16-bromohexadecyloxy)-t-butyldimethylsilane in tetrahydrofuran, and 0.20 ml of 1,4-dioxane were added to this solution at 0° C. The reaction mixture was refluxed for 24 hours while stirring. Saturated ammonium chloride solution was added to the reaction mixture, which was then extracted three times with dichloromethane. The organic layer was washed with saline solution and dried over magnesium sulfate, and the solvent was distilled off under reduced pressure. Purification of the residue by silica gel chromatography (heptane:ethyl acetate=7:3) gave [16-(t-butyldimethylsilanyloxy)hexadecyl]-(2,5-dimethoxyphenyl)amine as a yellow oil at a 50% yield.

Molecular weight: 479.1 ($C_{37}H_{57}NO_3Si$)
TLC: (heptane-ethyl acetate 7-3) Rf value=0.8
$^1$H-NMR: (300 MHz, CDCl$_3$) δ: 0.03 (s, 6H, —Si—(CH$_3$)$_2$); 0.88 (s, 9H, —Si-tBu); 1.26 (s large, 24H, —(CH$_2$)$_{12}$—); 1.49 (qt, 2H, J=6.7 Hz, —CH$_2$—); 1.63 (qt, 2H, J=7.2 Hz, —CH$_2$—); 3.07 (t, 2H, J=7.2 Hz, —CH$_2$—N); 3.58 (t, 2H, J=6.6 Hz, —CH$_2$—O); 3.74 (s, 3H, —OCH$_3$); 3.78 (s, 3H, —OCH$_3$); 4.50 (s large, 1H, —NH—); 6.14 (dd, 1H, J$^3$=8.7 Hz, J$^5$=3 Hz, aromatic-CH); 6.23 (d, 1H, J$^5$=3 Hz, aromatic-CH); 6.64 (d, 1H, J$^3$=8.7 Hz, aromatic-CH)
$^{13}$C-NMR: (75 MHz, CDCl$_3$) δ: −5.20; 18.30; 25.82; 25.85; 25.92; 28.14-29.55; 30.94; 42.87; 55.51; 56.01; 63.35; 98.39; 99.05; 114.35; 138.50; 141.56; 155.23

Synthesis Example C-(21)

[16-(t-Butyldimethylsilanyloxy)hexadecyl]-(2,5-dimethoxyphenyl)amine (144.2 mg) was dissolved in tetrahydrofuran, and then tetrabutylammonium fluoride (1 M solution in THF) (3.4 ml) was added to this solution. The reaction mixture was stirred for one day at room temperature. Saturated ammonium chloride solution was added to the reaction mixture, which was then extracted three times with diethyl ether. The organic layer was washed with saline solution and dried over magnesium sulfate, and the solvent was distilled off at reduced pressure. Purification of the residue by silica gel flash chromatography (heptane:ethyl acetate=6:4) gave 16-(2,5-dimethoxyphenylamino)hexadecan-1-ol as white crystals at an 81% yield.

Molecular weight: 393.60 ($C_{24}H_{43}NO_3$)
TLC: (heptane-ethyl acetate 6-4) Rf value=0.5
$^1$H-NMR: (300 MHz, CDCl$_3$) δ: 1.26 (s large, 24H, —(CH$_2$)$_{12}$—); 1.52 (qt, 2H, J=6.6 Hz, —CH$_2$—); 1.63 (qt, 2H, J=6.9 Hz, —CH$_2$—); 3.05 (t, 2H, J=7.2, —CH$_2$—N); 3.60 (t, 2H, J=6.6 Hz, —CH$_2$—O—); 3.72 (s, 3H, —OCH$_3$); 3.76 (s, 3H, —OCH$_3$); 4.50 (s large, 1H, —NH—); 6.10 (dd, 1H, J$^3$=8.4 Hz, J$^5$=2.7 Hz, aromatic-CH); 6.19 (d, 1H, J$^5$=2.7 Hz, aromatic-CH); 6.62 (d, 1H, J$^3$=8.4 Hz, aromatic-CH)
$^{13}$C-NMR: (75 MHz, CDCl$_3$) δ: 25.73; 27.18-29.64; 32.82; 44.10; 55.53; 56.04; 63.10; 99.50; 99.95; 109.99; 139.05; 143.57; 155.45

Synthesis Example C-(22)

14-(2,5-Dimethoxyphenylamino)tetradecan-1-ol was obtained by a method similar to Synthesis Example C-(21).

Molecular weight: 365.55 ($C_{22}H_{39}NO_3$)
TLC: (heptane-ethyl acetate 6-4) Rf value=0.5
$^1$H-NMR: (300 MHz, CDCl$_3$) δ: 1.26 (s large, 20H, —(CH$_2$)$_{10}$—); 1.52 (qt, 2H, J=6.6 Hz, —CH$_2$—); 1.63 (qt, 2H, J=6.9 Hz, —CH$_2$—); 3.05 (t, 2H, J=7.2, —CH$_2$—N); 3.60 (t, 2H, J=6.6 Hz, —CH$_2$—O—); 3.72 (s, 3H, —OCH$_3$); 3.76 (s, 3H, —OCH$_3$); 4.50 (s large, 1H, —NH—); 6.10 (dd, 1H, J$^3$=8.4 Hz, J$^5$=2.7 Hz, aromatic-CH); 6.19 (d, 1H, J$^5$=2.7 Hz, aromatic-CH); 6.62 (d, 1H, J$^3$=8.4 Hz, aromatic-CH)
$^{13}$C-NMR: (75 MHz, CDCl$_3$) δ: 25.73; 27.18-29.64; 32.82; 44.10; 55.53; 56.04; 63.10; 99.50; 99.95; 109.99; 139.05; 143.57; 155.45

Synthesis Example C-(23)

12-(2,5-Dimethoxyphenylamino)dodecan-1-ol was obtained by a method similar to Synthesis Example C-(21).

Molecular weight: 337.50 ($C_{20}H_{35}NO_3$)
TLC: (heptane-ethyl acetate 6-4) Rf value=0.5
$^1$H-NMR: (300 MHz, CDCl$_3$) δ: 1.26 (s large, 16H, —(CH$_2$)$_8$—); 1.52 (qt, 2H, J=6.6 Hz, —CH$_2$—); 1.63 (q, 2H, J=6.9 Hz, —CH$_2$—); 3.05 (t, 2H, J=7.2, —CH$_2$—N); 3.60 (t, 2H, J=6.6 Hz, —CH$_2$—O—); 3.72 (s, 3H, —OCH$_3$); 3.76 (s, 3H, —OCH$_3$); 4.50 (s large, 1H, —NH—); 6.10 (dd, 1H, J$^3$=8.4 Hz, J$^5$=2.7 Hz, aromatic-CH); 6.19 (d, 1H, J$^5$=2.7 Hz, aromatic-CH); 6.62 (d, 1H, J$^3$=8.4 Hz, aromatic-CH)
$^{13}$C-NMR: (75 MHz, CDCl$_3$) δ: 25.73; 27.18-29.64; 32.82; 44.10; 55.53; 56.04; 63.10; 99.50; 99.95; 109.99; 139.05; 143.57; 155.45

Synthesis Example C-(24)

10-(2,5-Dimethoxyphenylamino)decan-1-ol was obtained by a method similar to Synthesis Example C-(21).

Molecular weight: 309.44 ($C_{18}H_{31}NO_3$)
TLC: (heptane-ethyl acetate 6-4) Rf value=0.5
$^1$H-NMR: (300 MHz, CDCl$_3$) δ: 1.26 (s large, 12H, —(CH$_2$)$_6$—); 1.52 (qt, 2H, J=6.6 Hz, —CH$_2$—); 1.63 (qt, 2H, J=6.9 Hz, —CH$_2$—); 3.05 (t, 2H, J=7.2, —CH$_2$—N); 3.60 (t, 2H, J=6.6 Hz, —CH$_2$—O—); 3.72 (s, 3H, —OCH$_3$); 3.76 (s, 3H, —OCH$_3$); 4.50 (s large, 1H, —NH—); 6.10 (dd, 1H, J$^3$=8.4 Hz, J$^5$=2.7 Hz, aromatic-CH); 6.19 (d, 1H, J$^5$=2.7 Hz, aromatic-CH); 6.62 (d, 1H, J$^3$=8.4 Hz, aromatic-CH)
$^{13}$C-NMR: (75 MHz, CDCl$_3$) δ: 25.73; 27.18-29.64; 32.82; 44.10; 55.53; 56.04; 63.10; 99.50; 99.95; 109.99; 139.05; 143.57; 155.45

Synthesis Example D-(25)

1,14-Tetradecandiol (1.5 g) was dissolved in 16.5 ml of cyclohexane, and 57% aqueous hydrobromic acid solution (16.5 ml) was added to this solution. The reaction mixture was refluxed for six hours while stirring. After the reaction, the mixture was extracted three times with diethyl ether. The organic layer was neutralized with saturated sodium hydrogen carbonate solution, washed with saline solution, dried over magnesium sulfate, and filtered, and the solvent was distilled off under reduced pressure. Purification of the residue by silica gel flash chromatography (hexane:ethyl acetate=7:3) gave 14-bromotetradecan-1-ol as white crystals at a 67% yield.

Molecular weight: 292.90 ($C_{14}H_{29}BrO$)

TLC: (hexane-ethyl acetate 7-3) Rf value=0.53

$^1$H-NMR: (300 MHz, CDCl$_3$) δ: 1.26 (s large, 20H, —(CH$_2$)$_{10}$—); 1.56 (qt, 2H, J=7.0 Hz, —CH$_2$—); 1.85 (qt, 2H, J=7.1 Hz, —CH$_2$—); 3.40 (t, 2H, J=6.9 Hz, —CH$_2$—Br); 3.64 (t, 2H, J=6.6 Hz, —CH$_2$—O—)

$^{13}$C-NMR: (75 MHz, CDCl$_3$) δ: 25.72; 28.17; 28.75; 29.41-32.80; 32.82; 34.05; 63.08

Synthesis Example D-(26)

2,5-Dimethoxybenzaldehyde (5 g) was dissolved in 200 ml of dichloromethane, and m-chloroperbenzoic acid (mCPBA) (8.77 g) was added to this solution at 0° C. in small portions. The reaction mixture was stirred at room temperature for 24 hours. The reaction mixture was neutralized using sodium thiosulfate (200 ml), and then extracted three times with dichloromethane. The organic layer was washed with distilled water and then with saline solution, and dried over magnesium sulfate, and then the solvent was distilled off under reduced pressure. The obtained reddish oil was saponified with 50 ml of 10% aqueous sodium hydroxide (NaOH) solution. Next, the reaction mixture was acidified with 37% hydrochloric acid (HCl), and then neutralized with sodium hydrogen carbonate. It was then extracted three times with diethyl ether. The organic layer was washed with saline solution and dried over magnesium sulfate, and the solvent was distilled off under reduced pressure. This gave 2,5-dimethoxyphenol as a yellow oil. The purity of this oil was such that it did not require purification, and the yield was 90%.

Molecular weight: 154.17 ($C_8H_{10}O_3$)

TLC: (heptane-Et$_2$O 5-5) Rf value=0.35

$^1$H-NMR: (300 MHz, CDCl$_3$) δ: 3.75 (s, 3H, —OCH$_3$); 3.84 (s, 3H, —OCH$_3$); 6.37 (dd, 1H, J$^3$=8.7 Hz, J$^5$=3.0 Hz, aromatic-CH); 6.56 (d, 1H, J$^5$=3.0 Hz, aromatic-CH); 6.76 (d, 1H, J$^3$=8.7 Hz, aromatic-CH)

$^{13}$C-NMR: (75 MHz, CDCl$_3$) δ: 55.65; 56.57; 101.73; 104.23; 111.46; 140.95; 146.42; 154.56

Synthesis Example D-(27)

2,5-Dimethoxyphenol (287.1 mg) was dissolved in 30 ml of acetone, and to this solution, potassium carbonate and a solution of 14-bromotetradecan-1-ol (599.5 g) in 2 ml of acetone were added. The reaction mixture was stirred at reflux temperature (56° C.) for 24 hours, and then neutralized with saturated ammonium chloride solution. It was then extracted three times with diethyl ether. The organic layer was washed with saline solution and dried over magnesium sulfate, and then the solvent was distilled off under reduced pressure. Purification of the residue by silica gel chromatography (eluting with dichloromethane) gave 14-(2,5-dimethoxyphenoxy)tetradecan-1-ol as white crystals at a 65% yield.

Molecular weight: 366.53 ($C_{22}H_{38}O_4$)

TLC: (CH$_2$Cl$_2$ 100%) Rf value=0.2

$^1$H-NMR: (300 MHz, CDCl$_3$) δ: 1.26 (s large, 20H, —(CH$_2$)$_{10}$—); 1.54 (qt, 2H, J=6.9 Hz, —CH$_2$—); 1.81 (qt, 2H, J=7.2 Hz, —CH$_2$—); 3.63 (t, 2H, J=6.6 Hz, —CH$_2$—OH); 3.76 (s, 3H, —OCH$_3$); 3.81 (s, 3H, —OCH$_3$); 3.97 (t, 2H, J=6.9 Hz, —CH$_2$—O-Ph); 6.38 (dd, 1H, J$^3$=8.7 Hz, J$^5$=2.8 Hz, aromatic-CH); 6.50 (d, 1H, J$^5$=2.8 Hz, aromatic-CH); 6.78 (d, 1H, J$^3$=8.7 Hz, aromatic-CH)

$^{13}$C-NMR: (75 MHz, CDCl$_3$) δ: 25.75; 25.97-32.5; 32.83; 55.67; 56.81; 63.12; 68.96; 101.66; 103.01; 112.66; 144.41; 151.08; 155.44

Synthesis Example D-(28)

The compound, 10-(2,5-dimethoxyphenoxy)decan-1-ol, was obtained as white crystals at a 95% yield by a method similar to Synthesis Example D-(27).

Molecular weight: 310.43 ($C_{18}H_{30}O_4$)

TLC: (CH$_2$Cl$_2$ 100%) Rf value=0.2

$^1$H-NMR: (300 MHz, CDCl$_3$) δ: 1.26 (s large, 12H, —(CH$_2$)$_6$—); 1.54 (qt, 2H, J=6.9 Hz, —CH$_2$—); 1.81 (qt, 2H, J=7.2 Hz, —CH$_2$—); 3.63 (t, 2H, J=6.6 Hz, —CH$_2$—OH); 3.76 (s, 3H, —OCH$_3$); 3.81 (s, 3H, —OCH$_3$); 3.97 (t, 2H, J=6.9 Hz, —CH$_2$—O-Ph); 6.38 (dd, 1H, J$^3$=8.7 Hz, J$^5$=2.8 Hz, aromatic-CH); 6.50 (d, 1H, J$^5$=2.8 Hz, aromatic-CH); 6.78 (d, 1H, J$^3$=8.7 Hz, aromatic-CH)

$^{13}$C-NMR: (75 MHz, CDCl$_3$) δ: 25.72; 25.94-29.53; 32.80; 55.65; 56.78; 63.10; 68.93; 101.64; 102.99; 112.65; 143.83; 149.56; 154.27

Synthesis Example D-(29)

The compound, 12-(2,5-dimethoxyphenoxy)dodecan-1-ol, was obtained as white crystals at a 94% yield by a method similar to Synthesis Example D-(27).

Molecular weight: 338.25 ($C_{20}H_{34}O_4$)

TLC: (CH$_2$Cl$_2$ 100%) Rf value=0.2

$^1$H-NMR: (300 MHz, CDCl$_3$) δ: 1.26 (s large, 16H, —(CH$_2$)$_8$—); 1.54 (qt, 2H, J=6.9 Hz, —CH$_2$—); 1.81 (qt, 2H, J=7.2 Hz, —CH$_2$—); 3.63 (t, 2H, J=6.6 Hz, —CH$_2$—OH); 3.76 (s, 3H, —OCH$_3$); 3.81 (s, 3H, —OCH$_3$); 3.97 (t, 2H, J=6.9 Hz, —CH$_2$—O-Ph); 6.38 (dd, 1H, J$^3$=8.7 Hz, J$^5$=2.8 Hz, aromatic-CH); 6.50 (d, 1H. J$^5$=2.8 Hz, aromatic-CH); 6.78 (d, 1H, J$^3$=8.7 Hz, aromatic-CH)

$^{13}$C-NMR: (75 MHz, CDCl$_3$) δ: 25.71; 25.92-29.91; 32.77; 55.61; 56.76; 62.99; 68.89; 101.63; 102.65; 112.65; 143.82; 149.54; 154.26.

Synthesis Example D-(30)

The compound, 16-(2,5-dimethoxyphenoxy)hexadecan-1-ol was obtained as white crystals at a 62% yield by a method similar to Synthesis Example D-(27).

Molecular weight: 394.17 ($C_{24}H_{42}O_4$)

TLC: (CH$_2$Cl$_2$ 100%) Rf value=0.2

$^1$H-NMR: (300 MHz, CDCl$_3$) δ: 1.26 (s large, 24H, —(CH$_2$)$_{12}$—); 1.54 (qt, 2H, J=6.9 Hz, —CH$_2$—); 1.81 (qt, 2H, J=7.2 Hz, —CH$_2$—); 3.63 (t, 2H, J=6.6 Hz, —CH$_2$—OH); 3.76 (s, 3H, —OCH$_3$); 3.81 (s, 3H, —OCH$_3$); 3.97 (t, 2H, J=6.9 Hz, —CH$_2$—O-Ph); 6.38 (dd, 1H, J$^3$=8.7 Hz, J$^5$=2.8 Hz, aromatic-CH); 6.50 (d, 1H, J$^5$=2.8 Hz, aromatic-CH); 6.78 (d, 1H, J$^3$=8.7 Hz, aromatic-CH)

$^{13}$C-NMR: (75 MHz, CDCl$_3$) δ: 25.76; 25.97-32.66; 32.84; 55.67; 56.81; 63.13; 68.96; 101.65; 103.01; 112.66; 144.41; 151.08; 155.44

Synthesis Example E-(31)

12-(2,5-Dimethoxyphenyl)dodecan-1-ol (50 mg) was dissolved in 1 ml of dichloromethane, and boron tribromide (BBr$_3$) (146.6 µl) was added to this solution at −78° C. After stirring the reaction mixture at room temperature for one hour, this was cooled to −78° C., and the reaction was quenched with water and diethyl ether. The reaction mixture was extracted three times with diethyl ether. The organic layer was washed with saline solution and dried over magnesium sulfate, and the solvent was distilled off under reduced pressure. This gave 2-(12-hydroxydodecyl)benzene-1,4-diol as white crystals. The purity of the crystals was such that it did not require further purification, and the yield was 95%.

Molecular weight: 294.43 ($C_{18}H_{42}O_3$)
TLC: (heptane-ethyl acetate 5-5) Rf value=0.41
$^1$H-NMR: (300 MHz, $CD_3OD$) δ: 1.29 (s large, 16H, —$(CH_2)_8$—); 1.50 (qt, 4H, J=6.6 Hz, —$CH_2$—); 2.49 (t, 2H, J=7.6 Hz, —$CH_2$—Ar); 3.53 (t, 2H, J=6, 6 Hz, —$CH_2$—O—); 4.85 (s, 3H, —OH); 6.42 (dd, 1H, $J^3$=8.5 Hz, $J^5$=3.0 Hz, aromatic-CH); 6.51 (d, 1H, $J^5$=3.0 Hz, aromatic-CH); 6.56 (d, 1H, $J^3$=8.5 Hz, aromatic-CH)
$^{13}$C-NMR: (300 MHz, $CD_3OD$) δ: 25.52; 29.17-29.63; 29.83; 32.24; 61.60; 112.41; 115.18; 116.16; 129.94; 147.64; 149.52

Synthesis Example E-(32)

The compound, 2-(18-hydroxyoctadecyl)benzene-1,4-diol, was obtained as white crystals at a 95% yield by a method similar to Synthesis Example (31).

Molecular weight: 378.59 ($C_{24}H_{42}O_3$)
TLC (heptane-ethyl acetate 5-5) Rf value=0.41
$^1$H-NMR: (75 MHz, $CD_3OD$) δ: 1.29 (s large, 28H, —$(CH_2)_{14}$—); 1.50 (qt, 4H, J=6.6 Hz, —$CH_2$—); 2.49 (t, 2H, J=7.6 Hz, —$CH_2$—Ar); 3.53 (t, 2H, J=6, 6 Hz, —$CH_2$—O—); 4.85 (s, 3H, —OH); 6.42 (dd, 1H, $J^3$=8.5 Hz, $J^5$=3.0 Hz, aromatic-CH); 6.51 (d, 1H, $J^5$=3.0 Hz, aromatic-CH); 6.56 (d, 1H, $J^3$=8.5 Hz, aromatic-CH)
$^{13}$C-NMR: (75 MHz, $CD_3OD$) δ: 25.52; 29.17-29.63; 29.83; 32.24; 61.60; 112.41; 115.18; 116.16; 129.94; 147.64; 149.53

Synthesis Example E-(33)

The compound, 2-hexadecylbenzene-1,4-diol was obtained as white crystals at a 95% yield by a method similar to Synthesis Example (31).

Molecular weight: 334.54 ($C_{22}H_{38}O_2$)
TLC (heptane-ethyl acetate) Rf value=0.40
$^1$H-NMR: (300 MHz, $CD_3OD$) δ: 0.88 (t, 3H, J=6.7 Hz, —$CH_3$); 1.27 (s large, 26H, —$(CH_2)_{13}$—); 1.50 (qt, 2H, J=6.6 Hz, —$CH_2$—); 2.49 (t, 2H, J=7.6 Hz, —$CH_2$—Ar); 4.83 (s, 2H, —OH); 6.43 (dd, 1H, $J^3$=8.5 Hz, $J^5$=3.3 Hz, aromatic-CH); 6.51 (d, 1H, $J^5$=3.3 Hz, aromatic-CH); 6.56 (d, 1H, $J^3$=8.5 Hz, aromatic-CH)
$^{13}$C-NMR: (75 MHz, $CD_3OD$) δ: 13.18; 22.36; 22.93; 29.09-29.67; 29.89; 31.68; 112.45; 115.26; 116.21; 130.04; 147.62; 149.48

Synthesis Example E-(34)

The compound, 2-(15-hydroxypentadecyl)benzene-1,4-diol was obtained as white crystals by a method similar to Synthesis Example (31).

Antioxidant Activity Test

Example 1A

The ability of the derivatives obtained in preparation processes A and B to scavenge 2,2-diphenyl-1-picrylhydrazyl (DPPH) (active organic radical species scavenging ability) was measured by the following method.

Trolox® and the test compounds were individually dissolved in ethanol and the solutions were adjusted to a final concentration of 10 mM. Next, each solution was diluted severalfold to obtain solutions at concentrations ranging from 10 mM to 1 μM.

100 μl of each of the obtained ethanol solutions was added to a multi-well ELISA plate along with 100 μl of 400 μM DPPH solution in ethanol. The absorbance (optical density, OD) at 550 nm was measured for these solutions.

DPPH scavenging ability was determined for each test compound based on the results of these measurements. For comparison, the test compound solutions in ethanol were substituted with ethanol alone.

The scavenging ability of each test compound is presented as a percent decrease in OD with respect to the absorbance of the comparative sample. The results are shown in Table 1.

TABLE 1

Results of DPPH scavenging ability test on the compounds of the present invention

| Product | $IC_{50}$ (mM) |
|---|---|
| Trolox ® | 0.23 |
| Compound of Synthesis Example A-(5) | >10 mM |
| Compound of Synthesis Example A-(9) | >10 mM |
| Compound of Synthesis Example A- | >10 mM |
| Compound of Synthesis Example E-(31) | 0.23 |

TABLE 1-continued

Results of DPPH scavenging ability test on the compounds of the present invention

| Product | IC$_{50}$ (mM) |
|---|---|
| 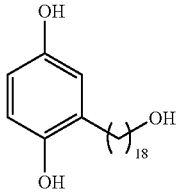 Compound of Synthesis Example E-(32) | 0.23 |
| 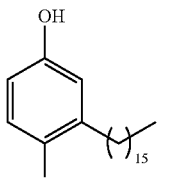 Compound of Synthesis Example E-(33) | 1.53 |
| 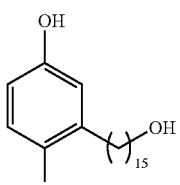 Compound of Synthesis Example E-(34) | 0.23 |
| 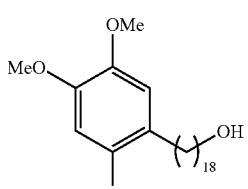 Compound of Synthesis Example B-(17) | >10 mM |
| 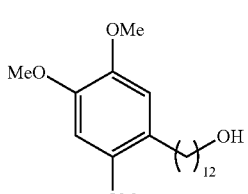 Compound of Synthesis Example B-(14) | >10 mM |

As is clear from Table 1, demethylated compounds have excellent DPPH scavenging ability as compared to Trolox®. Methylated compounds either do not have scavenging ability or their scavenging ability is at a level that cannot be detected by the DPPH test.

Example 2A

Hydroxyl radical scavenging ability was measured for derivatives obtained in preparation processes A, B, and E by the following method using an ABTS (2,2'-azinobis(3-ethyl-benzthiazolin-6-sulfonic acid)) scavenging assay.

In this test, hydroxyl radicals were generated in situ by the Fenton reaction. Next, competitive reactions between ABTS and the test compounds took place, and the hydroxyl radicals were scavenged by ABTS to form ABTS$^+$ radical cations, or were scavenged by the test compounds.

The test compounds and Trolox® were individually dissolved in ethanol and the solutions were adjusted to a final concentration of 10 mM. Each solution was then diluted severalfold to obtain solutions at concentrations ranging from 10 mM to 1 μM.

Next, 180 μl of 1:1 ethanol-water solution was added to a multi-well ELISA plate, and then 30 μl of 1 mM aqueous ABTS solution, 30 μl of 0.5 mM aqueous Fe$_2$SO$_4$ solution, 30 μl of a solution of each test compound in ethanol, and 30 μl of 100 mM aqueous hydrogen peroxide solution were added. The obtained solutions were left to stand for 45 minutes at room temperature, and the absorbance (OD) at 405 nm was measured. OH radical scavenging ability was determined for each test compound based on the results of these measurements. For comparison, the test compound solutions in ethanol were substituted with ethanol alone. The results are shown in Table 2.

TABLE 2

Results of OH radical scavenging ability test on the compounds of the present invention

| Product | IC$_{50}$ (μM) |
|---|---|
| Trolox® | 600 μM |
| 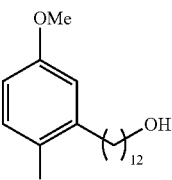 Compound of Synthesis Example A-(5) | >10 mM |
| 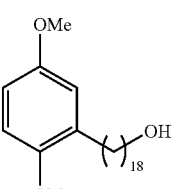 Compound of Synthesis Example A-(9) | >10 mM |
| 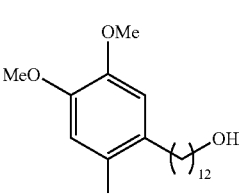 Compound of Synthesis Example B-(14) | 720 μM |
| 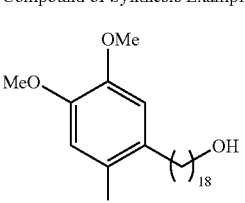 Compound of Synthesis Example B-(17) | 720 μM |

TABLE 2-continued

Results of OH radical scavenging ability test on the compounds of the present invention

| Product | IC$_{50}$ (μM) |
|---|---|
| 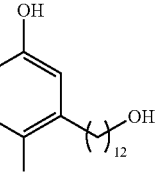 Compound of Synthesis Example E-(31) | 6 μM |
| 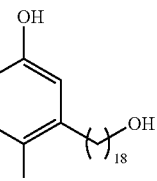 Compound of Synthesis Example E-(32) | 6 μM |
| 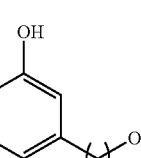 Compound of Synthesis Example E-(34) | 6 μM |

As is clear from Table 2, demethylated hydroquinones do not have scavenging ability towards hydroxyl radicals. Trimethylated trihydroquinones have scavenging ability equivalent to that of Trolox®. Dihydroquinones were found to be compounds with scavenging ability 100 times higher than that of Trolox®.

Example 3A

Tests similar to those in Examples 1 and 2 were carried out on the other compounds obtained in Synthesis Examples of the present invention. These results are shown in Tables 3 and 4. The test results of Examples 1 and 2 are also indicated in these Tables. As can be seen from the Tables, the results were similar to those in Examples 1 and 2.

Table 3, Table 4: Results of DPPH Scavenging Ability Tests and OH Radical Scavenging Ability Tests on the Compounds of the Present Invention

TABLE 3

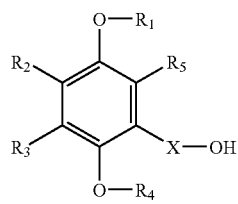

(1)

| Synthesis Example | 5 | 6 | 7 | 8 | 9 | 13 | 14 | 15 | 16 | 17 |
|---|---|---|---|---|---|---|---|---|---|---|
| R$_1$ | Me | Me | Me | Me | Me | Me | Me | Me | Me | Me |
| R$_2$ | H | H | H | H | H | MeO | MeO | MeO | MeO | MeO |
| R$_3$ | H | H | H | H | H | H | H | H | H | H |
| R$_4$ | Me | Me | Me | Me | Me | Me | Me | Me | Me | Me |
| R$_5$ | H | H | H | H | H | H | H | H | H | H |
| X | 12 | 14 | 15 | 16 | 18 | 14 | 12 | 15 | 16 | 18 |
| DPPH test | – | – | – | – | – | – | – | – | – | – |
| OH test | – | – | – | – | – | ++ | ++ | ++ | ++ | ++ |

+: effective; –: >10 mM

TABLE 4

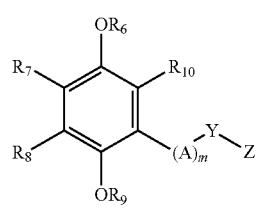

(2)

| Synthesis Example | 21 | 22 | 23 | 24 | 29 | 30 | 31 | 32 | 33 | 34 |
|---|---|---|---|---|---|---|---|---|---|---|
| R$_6$ | Me | Me | Me | Me | Me | Me | H | H | H | H |
| R$_7$ | H | H | H | H | H | H | H | H | H | H |
| R$_8$ | H | H | H | H | H | H | H | H | H | H |
| R$_9$ | Me | Me | Me | Me | Me | Me | H | H | H | H |
| R$_{10}$ | H | H | H | H | H | H | H | H | H | H |
| A | N | N | N | N | O | O | none | none | none | none |
| Y | 16 | 14 | 12 | 10 | 12 | 16 | 12 | 18 | 16 | 15 |
| Z | OH | OH | OH | OH | OH | OH | OH | OH | H | OH |
| DPPH test | – | – | – | – | – | – | ++ | ++ | + | ++ |
| OH test | – | – | – | – | – | – | ++ | ++ | + | ++ |

+: effective; –: >10 mM

Toxicity and Biological Activity Tests

QFAs are stable in aqueous media used for cell cultures and were administered to cells in a methylated form so that they would be demethylated by a particular enzyme (O-demethylase) in the cells. This enables sufficient application of their nerve-protecting activity and radical scavenging ability.

Cytotoxicity Tests

The toxicity of all test compounds was examined using two types of cancer cell lines: C6 glioblastoma and B104 neuroblastoma.

Example 1B

C6 cells were plated at a concentration of $2 \times 10^5$ cells/well, and were cultured using a serun-containing medium (Dulbecco's modified Eagle medium, 10% fetal calf serum) in 5% $CO_2$ at 37° C. for 48 hours. On day 3, the medium was substituted with a chemically defined medium (Dulbecco's modified Eagle medium, 10 μg/ml holotransferrin, 5 μg/ml insulin, and 0.1% ethanol), test compounds were added at different concentrations ranging from $10^{-9}$ M to $10^{-6}$ M, and the cells were cultured again in 5% $CO_2$ at 37° C. for three days. The chemically defined medium was exchanged every 24 hours.

The cells were fixed with trichloroacetic acid (10% solution in deionized water) at 4° C. for 30 minutes, and then washed five times with deionized water. The plates were then dried for 24 hours. The cells were stained by treatment with 70 μl of sulforhodamine B solution (0.4% m/v solution in 1% acetic acid) for 20 minutes, and then washed five times with 1% acetic acid. The plates were dried for two hours, and the residual sulforhodamine B was removed with 10 mM tris base (100 μl). The plates were shaken for 15 minutes, and optical densities (ODs) at 492 nm and 620 nm were measured.

The toxicity of each test compound was determined based on the results of these measurements. For comparison, the test compound solutions in ethanol were substituted with pure ethanol.

The results of cytotoxicity tests of QFAs, Q3FAs, QoFAs, and QnFAs are shown in FIG. 1. These abbreviations indicate the following:
QFA: dimethoxyphenyl derivative
Q3FA: trimethoxyphenyl derivative
QoFA: phenoxy derivative
QnFA: phenylamino derivative The number following FA in the figure indicates the chain length (number of carbons) of the branched chain. Comparison of each of the test compounds by Student's test did not show significant differences.

The results shown in FIG. 1 showed that QFAs, Q3FAs, QoFAs, and QnFAs are not cytotoxic at the concentrations used for testing in cultured C6 cell line.

Example 2B

B104 cells were plated at a concentration of $2 \times 10^5$ cells/well, and were cultured using a serum-containing medium (Dulbecco's modified Eagle medium, 10% fetal calf serum) in 5% $CO_2$ at 37° C. for 48 hours. On day 3, the medium was substituted with a chemically defined medium (Dulbecco's modified Eagle medium, 10 μg/ml holotransferrin, 5 μg/ml insulin, and 0.1% ethanol), test compounds were added at different concentrations ranging from $10^{-9}$ M to $10^{-6}$ M, and the cells were cultured again in 5% $CO_2$ at 37° C. for three days. The chemically defined medium was exchanged every 24 hours.

The cells were fixed by treatment with trichloroacetic acid (10% solution in deionized water) at 4° C. for 30 minutes, and then washed five times with deionized water. The plates were then dried for 24 hours. The cells were stained by treatment with 70 μl of sulforhodamine B solution (0.4% m/v solution in 1% acetic acid) for 20 minutes, and then washed five times with 1% acetic acid. The plates were dried for two hours, and the residual sulforhodamine B was removed with 10 mM tris base (100 μl). The plates were shaken for 15 minutes, and optical densities (ODs) at 492 nm and 620 nm were measured.

The toxicity of each test compound was determined based on the results of these measurements. For comparison, the test compound solutions in ethanol were substituted with ethanol alone.

Figure 2:
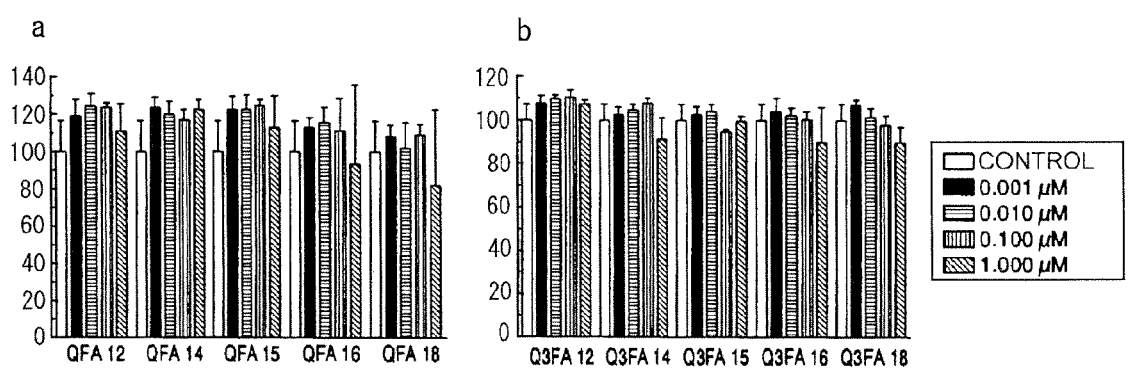
FIG. 2 shows graphs indicating the toxicity of QFAs to a cultured B104 cell line.

The results of the cytotoxicity tests of QFAs and Q3FAs are shown in FIG. 2. Comparison of each of the test compounds by Student's test did not show significant differences.

According to the results shown in FIG. 2, QFAs and Q3FAs are not cytotoxic at the concentrations used for testing in cultured B104 cell line.

Biological Activity

Primary Culture Cell Test

Example 1C

Culturing of CNS Neurons

Fetal mouse (15 days old) cerebral hemispheres were dissected in cold Gey's balanced salt solution supplemented with glucose to isolate the neocortex. Cells were dispersed by trypsin and mechanical dissociation. Next, the cells were plated at a concentration of 200,000 cells/well onto cover slips coated with 1 μg/ml of poly-L-lysine, and the cells were cultured in a serum-containing medium (Dulbecco's modified Eagle medium, 2 mM glutamine, 1 g/l glucose, 10% fetal calf serum, and penicillin/streptomycin) in 5% $CO_2$ at 37° C. for 24 hours.

On day 2, the medium was substituted with a chemically defined medium (Dulbecco's modified Eagle medium, 2 mM glutamine, 1 g/l glucose, 16 μg/ml putrescine, 52 ng/ml selenium, 10 μg/ml holotransferrin, 5 μg/ml insulin, and 3 ng/ml progesterone), and test compounds were added at different concentrations. The cells were cultured in 5% $CO_2$ at 37° C. for 24 hours.

Immunocytochemical Staining and Morphometric Analysis

On day 3, the cells were fixed with 4% formaldehyde in phosphate buffered saline (PBS) for ten minutes. After two washes with PBS, permeation of cells was performed with 100% methanol for five minutes. After five washes with PBS, the cells were stained for two hours with an anti-phosphoneurofilament antibody (Smi312) diluted 1/400 in PBS-bovine serum albumin (3%). Several washes with PBS were followed by a secondary immunostaining for 45 minutes in the dark with Alexa488-conjugated antibody diluted 1/200 in PBS. After two final washes with PBS, the plates were washed with water and mounted in Aqua-Polymount.

Photographs were randomly taken (×20 magnification) using an Axiovert 200 microscope (Zeiss) equipped with a digital camera. The axonal length of each neuron was determined using a computer-assisted image analyzer (UTHSCSA Image Tool 3.0).

The screening tests showed that the QFA series are most effective, and that QFA15 with a 15-carbon chain as its side chain is the most active compound.

Figure 3:
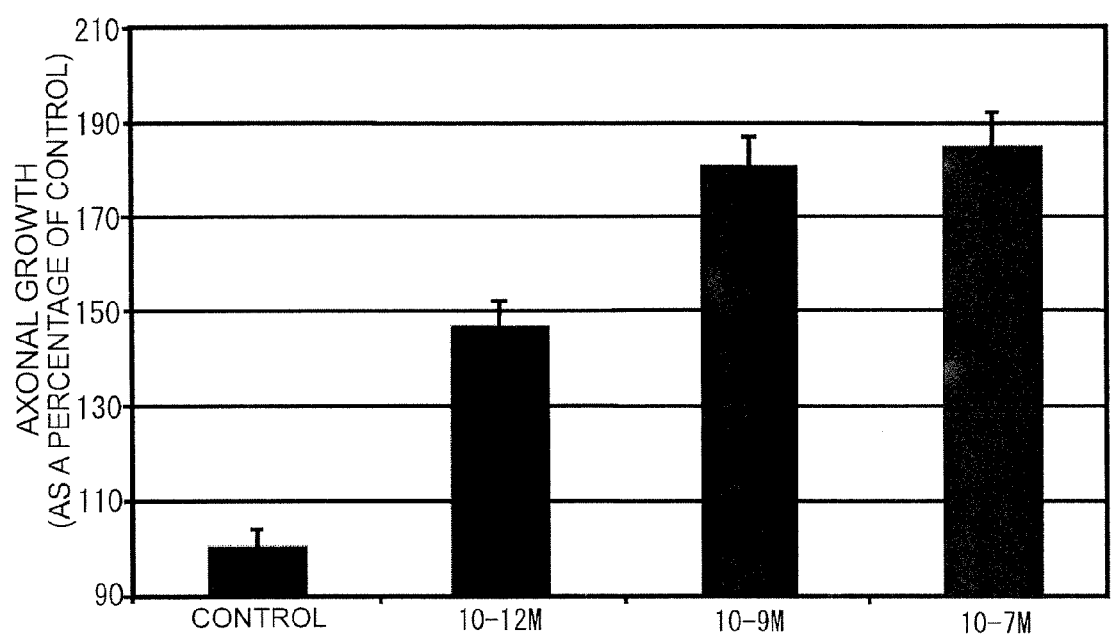
FIG. 3 shows a graph indicating the axonal growth-promoting activity of QFA15 on E15 neurons. The vertical axis indicates axonal growth (as a percentage of the control).
Figure 4:
FIG. 4 shows micrographs showing promoting effects, in particular, axonal growth-promoting effect of QFA15 on E15 neurons (85 μM control, 155 μM QFA15).
Figure 4:

FIGS. 3 and 4 show the effect of QFA15 on E15 neurons.

Figure 5:
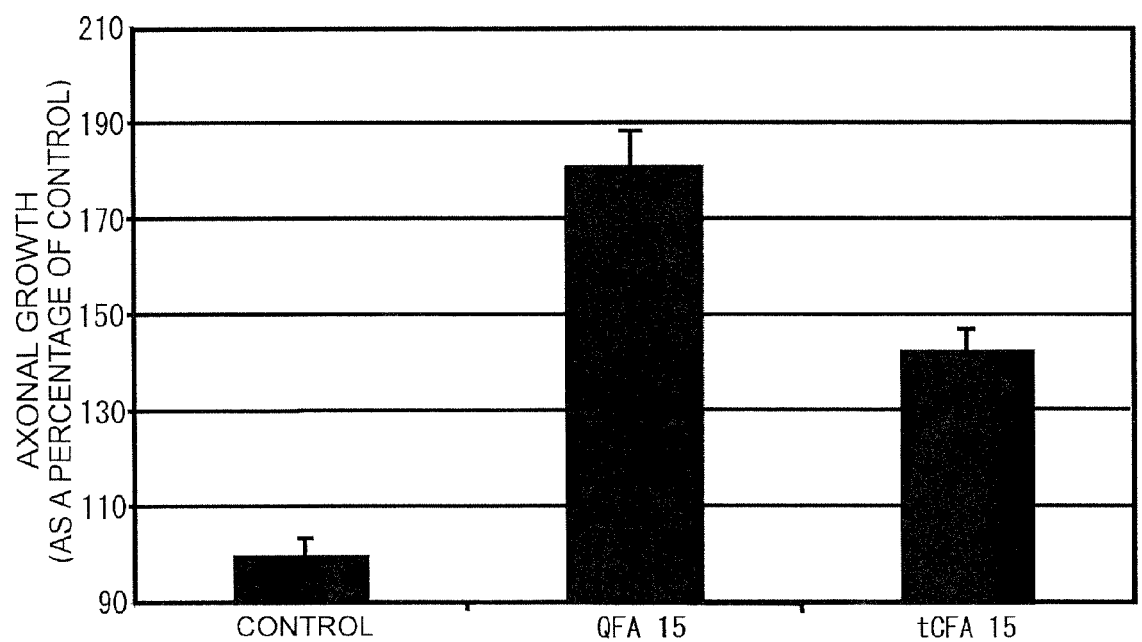
FIG. 5 shows a graph indicating axonal growth-promoting activity of QFA15 and tCFA15 ($10^{-9}$ M) on E15 neurons. The vertical axis indicates axonal growth (as a percentage of the control).
Figure 6:
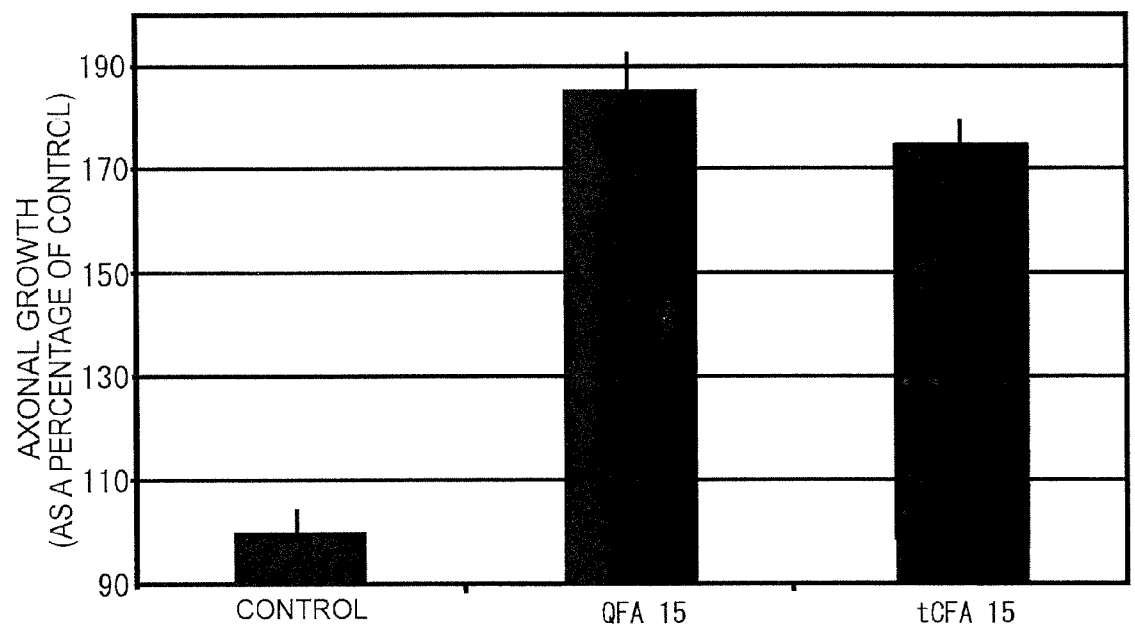
FIG. 6 shows a graph indicating axonal growth-promoting activity of QFA15 and tCFA 15 ($10^{-7}$ M) on E15 neurons. The vertical axis indicates axonal growth (as a percentage of the control).

In a previous study, a similar compound, 3-(15-hydroxypentadecyl)-2,4,4-trimethyl-2-cyclohexen-1-one (hereinafter, abbreviated as tCFA15; and synthesized by the method described in Patent Document 1) showed similar results (The Journal of Neurochemistry by Hanbali et al. (J. Neurochem., 90 (6), 1423-31, 2004)). Compared to tCFA15, QFA15 has greater axonal growth-promoting ability at a lower concentration. FIGS. 5 and 6 indicate these results.

The above-mentioned results show that QFA15 is an effective axonal growth-promoting agent that is bound to a strong antioxidant.

INDUSTRIAL APPLICABILITY

The compounds provided by the present invention, or salts thereof, have antioxidative activity or nerve growth-promoting activity and are nontoxic to living cells. Therefore, they will serve as antioxidants, nerve growth-promoting agents, or pharmaceuticals useful for the prevention or treatment of brain dysfunctions, motor dysfunctions, or urinary dysfunctions caused by the degeneration and/or loss of the central nervous system and peripheral nervous system neurons.

The invention claimed is:

1. A compound represented by the following formula (1), or a pharmaceutically acceptable salt of formula (1):

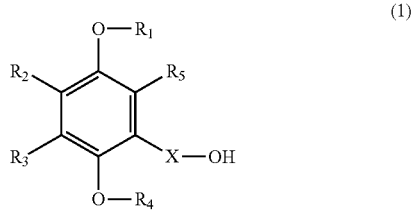

(1)

wherein,
$R_1$ and $R_4$ are each a methyl group;
$R_2$ is a hydrogen atom;
$R_3$ and $R_5$ are each a hydrogen atom; and
X represents an alkylene group with 10 to 20 carbons.

2. An antioxidant comprising as an active ingredient the compound of claim 1, including pharmaceutically acceptable salts of formula (1).

3. A nerve growth-promoting agent comprising as an active ingredient the compound of claim 1, including pharmaceutically acceptable salts of formula (1).

4. A therapeutic agent for treating a dysfunction caused by degeneration and/or loss of the central nervous system and/or peripheral nervous system neurons, which comprises as an active ingredient the compound of claim 1, including pharmaceutically acceptable salts of formula (1).

5. A compound represented by the following formula (2), or a pharmaceutically acceptable salt of formula (2):

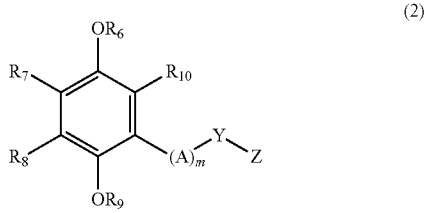

(2)

wherein,
$R_6$ and $R_9$ are each an alkyl group;
$R_7$ is a hydrogen atom or an alkoxy group;
$R_8$ and $R_{10}$ are each a hydrogen atom;
A represents an oxygen atom or NH, and m is 0 or 1; and
Y represents an alkylene group with 10 to 20 carbons, and Z represents a hydroxyl group.

6. The compound of claim 5, wherein $R_6$ and $R_9$ are each a methyl group, $R_7$ is a methoxy group, $R_8$ and $R_{10}$ are each a hydrogen atom, and m is 0.

7. The compound of claim 5, wherein $R_6$ and $R_9$ are each a methyl group, $R_7$, $R_8$ and $R_{10}$ are each a hydrogen atom, A is an oxygen atom, and m is 1.

8. The compound of claim 5, wherein $R_6$ and $R_9$ are each a methyl group, $R_7$, $R_8$ and $R_{10}$ are each a hydrogen atom, A is NH, and m is 1.

9. The compound of claim 5, wherein Y is an alkylene group with 12 carbons.

10. The compound of claim 5, wherein Y is an alkylene group with 18 carbons.

11. An antioxidant comprising as an active ingredient the compound of claim 5, including pharmaceutically acceptable salts of formula (2).

12. A nerve growth-promoting agent comprising as an active ingredient the compound of claim 5, including pharmaceutically acceptable salts of formula (2).

13. A therapeutic agent for treating a dysfunction caused by degeneration and/or loss of the central nervous system and/or peripheral nervous system neurons, which comprises as an active ingredient the compound of claim 5, including pharmaceutically acceptable salts of formula (2).

14. A method for treating a dysfunction caused by degeneration and/or loss of the central nervous system and/or peripheral nervous system neurons, wherein the method comprises the step of administering an effective amount of the compound of claim 1, including pharmaceutically acceptable salts of formula (1) to a patient who has a dysfunction caused by degeneration and/or loss of the central nervous system and/or peripheral nervous system neurons.

15. A method for preparing a therapeutic agent wherein said method comprises combining a compound of claim 1, including pharmaceutically acceptable salts of formula (1), with a pharmaceutically acceptable carrier.

16. A method for treating a dysfunction caused by degeneration and/or loss of the central nervous system and/or peripheral nervous system neurons, wherein the method comprises the step of administering an effective amount of the compound of claim 5, including pharmaceutically acceptable salts of formula (2), to a patient who has a dysfunction caused by degeneration and/or loss of the central nervous system and/or peripheral nervous system neurons.

17. A method for preparing a therapeutic agent wherein said method comprises combining a compound of claim 5, including pharmaceutically acceptable salts of formula (2), with a pharmaceutically acceptable carrier.

* * * * *